United States Patent
Yoon et al.

(10) Patent No.: US 11,230,505 B2
(45) Date of Patent: Jan. 25, 2022

(54) MICROBIAL CONSORTIA

(71) Applicant: AMVAC Chemical Corporation, Newport Beach, CA (US)

(72) Inventors: Sung-Yong H. Yoon, Lake Oswego, OR (US); Kathleen Swords, Boise, ID (US); D. Ry Wagner, Pleasant Hill, OR (US); Selvasundaram Rajagopal, New Delhi (IN)

(73) Assignee: AMVAC Chemical Corporation, Newport Beach, CA (US)

( * ) Notice: Subject to any disclaimer, the term of this patent is extended or adjusted under 35 U.S.C. 154(b) by 0 days.

(21) Appl. No.: 16/448,776

(22) Filed: Jun. 21, 2019

(65) Prior Publication Data

US 2019/0322601 A1 Oct. 24, 2019

Related U.S. Application Data

(62) Division of application No. 15/553,499, filed as application No. PCT/IB2016/051084 on Feb. 26, 2016, now abandoned.
(Continued)

(51) Int. Cl.
*A01N 59/04* (2006.01)
*C05F 11/08* (2006.01)
(Continued)

(52) U.S. Cl.
CPC .............. *C05F 11/08* (2013.01); *A01N 63/00* (2013.01); *A01N 63/10* (2020.01); *A01N 63/20* (2020.01);
(Continued)

(58) Field of Classification Search
CPC .......... C05F 11/08; C05F 17/20; C05F 1/002; C05F 1/007; C05G 3/60; C05G 5/20;
(Continued)

(56) References Cited

U.S. PATENT DOCUMENTS 8,445,255 B2 5/2013 Kloepper et al.
2011/0151508 A1 6/2011 Lopez-Cervantes et al.
(Continued)

FOREIGN PATENT DOCUMENTS

CN 1301310 A 6/2001
CN 101941762 A 1/2011
(Continued)

OTHER PUBLICATIONS

Pearce et al., "Metagenomic analysis of a southern maritime Antarctic soil," *Front Microbiol.*, vol. 3, Article 403, 2012 (13 pages).
(Continued)

*Primary Examiner* — David Browe
(74) *Attorney, Agent, or Firm* — Klarquist Sparkman, LLP

(57) ABSTRACT

Disclosed herein are microbial consortia and compositions including microbes, for example, for use in agricultural or biodegradation applications. In some embodiments, soil, plants, and/or plant parts (such as seeds, seedlings, shoots, roots, leaves, fruit, stems, or branches) are contacted with a disclosed microbial consortia or composition including microbes. The microbial consortia or microbe-containing compositions may be applied to soil, plant, and/or plant parts alone or in combination with additional components (such as chitin, chitosan, glucosamine, amino acids, and/or liquid fertilizer). In additional embodiments, the disclosed microbial consortia or compositions including microbes are used in methods of degrading biological materials, such as chitin-containing biological materials.

6 Claims, 15 Drawing Sheets

Specification includes a Sequence Listing.

Related U.S. Application Data

(60) Provisional application No. 62/126,337, filed on Feb. 27, 2015.

(51) Int. Cl.

| | | |
|---|---|---|
| *C12N 1/20* | (2006.01) | |
| *C12N 1/14* | (2006.01) | |
| *C05F 1/00* | (2006.01) | |
| *A01N 63/00* | (2020.01) | |
| *C05F 17/20* | (2020.01) | |
| *C05G 3/60* | (2020.01) | |
| *A01N 63/10* | (2020.01) | |
| *A01N 63/20* | (2020.01) | |
| *A01N 63/22* | (2020.01) | |
| *A01N 63/27* | (2020.01) | |
| *C12N 1/00* | (2006.01) | |
| *C05G 5/23* | (2020.01) | |
| *C05G 5/27* | (2020.01) | |
| *C12R 1/00* | (2006.01) | |

(52) U.S. Cl.
CPC ............ *A01N 63/22* (2020.01); *A01N 63/27* (2020.01); *C05F 1/002* (2013.01); *C05F 1/007* (2013.01); *C05F 17/20* (2020.01); *C05G 3/60* (2020.02); *C05G 5/23* (2020.02); *C05G 5/27* (2020.02); *C12N 1/00* (2013.01); *C12N 1/14* (2013.01); *C12N 1/20* (2013.01); *C12R 2001/00* (2021.05); *Y02A 40/20* (2018.01); *Y02E 50/30* (2013.01); *Y02P 20/145* (2015.11); *Y02W 30/40* (2015.05)

(58) Field of Classification Search
CPC . A01N 63/00; C12N 1/14; C12N 1/20; C12R 1/00; Y02W 30/40; Y02P 20/145; Y02A 40/20; Y02E 50/30
See application file for complete search history.

(56) References Cited

U.S. PATENT DOCUMENTS

| | | | |
|---|---|---|---|
| 2012/0084886 A1* | 4/2012 | Lopez-Cervantes ... | A01N 63/10 800/298 |
| 2013/0255338 A1* | 10/2013 | Lopez-Cervantes .... | C05F 11/08 71/7 |
| 2018/0235235 A1 | 8/2018 | Yoon et al. | |
| 2018/0235236 A1 | 8/2018 | Yoon et al. | |

FOREIGN PATENT DOCUMENTS

| | | |
|---|---|---|
| CN | 103857799 A | 6/2014 |
| RU | 2138551 C1 | 9/1999 |
| RU | 2197453 | 1/2003 |
| WO | WO 2011/076759 | 6/2011 |
| WO | WO 2011/157747 | 12/2011 |
| WO | WO 2012/037352 | 3/2012 |
| WO | WO 2013/148278 | 10/2013 |
| WO | WO 2017/131821 | 8/2017 |

OTHER PUBLICATIONS

Tomova et al., "Characterization of heavy metals resistant heterotrophic bacteria from soils in the Windmill Islands region, Wilkes Land, East Antarctica," *Polish Polar Research*, vol. 35, No. 4, pp. 597-604, 2014.

Brzezinska et al., "Chitinolytic microorganisms and their possible application in environmental protection." *Current Microbiology*, vol. 68, No. 1, pp. 71-81, 2014.

Bueno-Solano et al., "Chemical and biological characteristics of protein hydrolysates from fermented shrimp by-products," *Food Chemistry*, vol. 112, No. 3 pp. 671-675, 2009.

Declaration of Dr. Jaime Lopez-Cervantes, executed on Oct. 18, 2011, submitted in International App. No. PCT/EP2010/070285 dated Oct. 28, 2011 (2 pages).

* cited by examiner

Corn Trial Data (Iowa)

Tomato Trial 1 Data (California)

Tomato Trial 2 Data (California)

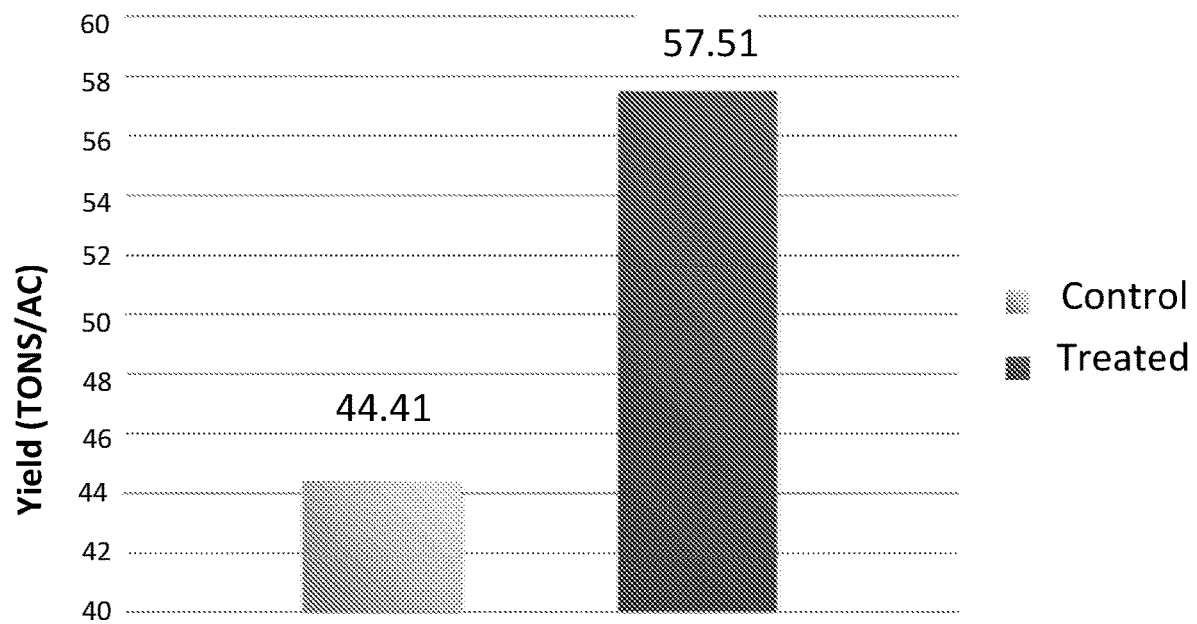

MICROBIAL CONSORTIA

CROSS REFERENCE TO RELATED APPLICATIONS

This is a divisional of co-pending U.S. application Ser. No. 15/553,499, filed Aug. 24, 2017, which claims the benefit of U.S. National Stage of International Application No. PCT/IB2016/051084, filed Feb. 26, 2016, which was published in English under PCT Article 21(2), which in turn claims the benefit of U.S. Provisional Application No. 62/126,337, filed Feb. 27, 2015, all of which are incorporated herein by reference in their entirety.

FIELD

This disclosure relates to microbial consortia and methods of use of the microbes included in the consortia, particularly for biodegradation and agricultural processes and uses.

BACKGROUND

World food demand continues to increase under pressure of increasing population growth. However, agricultural workers are faced with shrinking amounts of land available for agriculture, soil depletion, and changing environmental conditions, among other challenges. Thus, there is a need to develop compositions and techniques that can increase food production, while also decreasing the use of potentially harmful herbicides, insecticides, and fungicides.

SUMMARY

Disclosed herein are microbial consortia and compositions including microbes for use in agricultural or biodegradation applications. In some embodiments, a microbial composition of the present disclosure is the microbial consortium deposited with the American Type Culture Collection (ATCC, Manassas, Va.) on Nov. 25, 2014, and assigned deposit number PTA-121751 (also referred to herein as A1002) or a composition including some or all of the microbes in A1002. In other embodiments, a composition of the present disclosure includes microbes from five or more microbial species selected from *Bacillus* spp., *Azospirillum* spp., *Pseudomonas* spp., *Lactobacillus* spp., *Desulfococcus* spp., *Desulfotomaculum* spp., *Marinobacter* spp., *Nitrosopumilus* spp. *Ruminococcus* spp., *Aquabacterium* spp., *Acidisoma* spp., *Microcoleus* spp., *Clostridium* spp., *Xenococcus* spp., *Brevibacterium* spp., and *Methanosaeta* spp. In additional embodiments, the composition includes microbes from five or more (such as 5, 10, 15, or more) of the microbes listed in Table 1. The disclosed compositions may also include additional components, including but not limited to one or more of additional microbe species chitin, chitosan, glucosamine, and/or amino acids.

Also disclosed are agricultural uses of the disclosed microbial consortia or compositions. In some embodiments, the methods (uses) include contacting soil, plants, and/or plant parts (such as seeds, seedlings, roots, leaves, stems, or branches) with a disclosed microbial consortium (such as A1002), a composition including some or all of the microbes from A1002, or a composition including five or more of the microbial species listed in Table 1. The microbial consortia or microbe-containing compositions may be applied to soil, plant, and/or plant parts alone or in combination with additional components (such as additional microbes, chitin, chitosan, glucosamine, protein, amino acids, and/or soil supplements or fertilizer, such as liquid fertilizer).

In additional embodiments, the disclosed microbial consortia or compositions including microbes are used in methods of degrading biological materials, such as chitin-containing biological materials. In some examples, the chitin-containing materials are mixed with a microbial consortium (such as A1002) or a composition including five or more of the microbial species listed in Table 1 and fermented to produce a fermented mixture. The fermented mixture optionally may be separated into solid and liquid fractions. The fermented mixture or fractions produced therefrom can be used in agricultural applications in combination with the disclosed microbial consortia or compositions, or can be used in further degradation processes, for example to produce increased levels of degradation products in the fractions.

The foregoing and other features of the disclosure will become more apparent from the following detailed description, which proceeds with reference to the accompanying figures.

BRIEF DESCRIPTION OF THE DRAWINGS

FIG. 5D is a digital image showing roots of wheat plants treated with a microbial composition plus HYTb (test) compared to control plants.

FIGS. 6A-6E are a series of graphs showing the effect on yield of treatment of tomato with a microbial composition.

SEQUENCE LISTING

Figure 1:
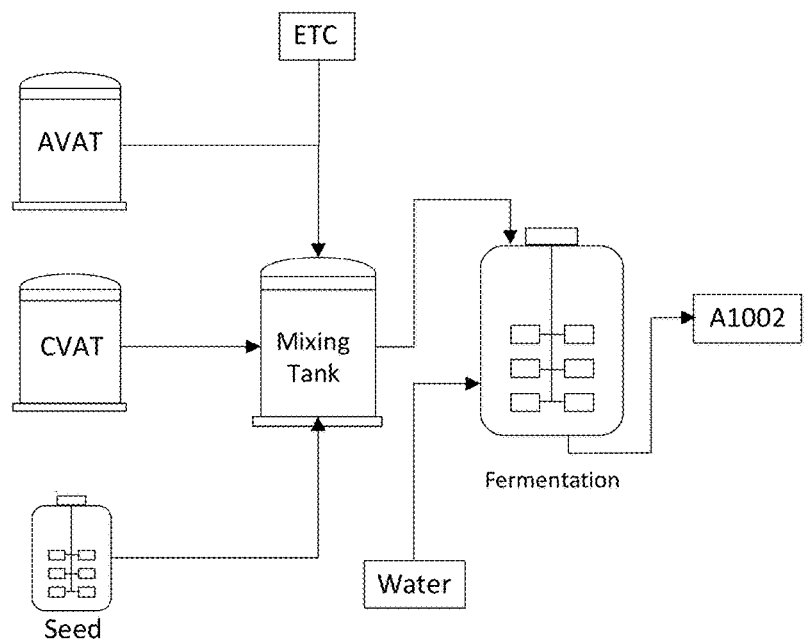
FIG. 1 is a schematic showing an exemplary fermentation process used to obtain the A1002 microbial consortium.

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Jun. 21, 2019, and is ~815 bytes, which is incorporated by reference herein.

SEQ ID NOs: 1 and 2 are forward and reverse primers, respectively, used to amplify 16S rDNA from A1002.

DETAILED DESCRIPTION

In nature, the balance of microbial species in the soil is influenced by soil type, soil fertility, moisture, competing microbes, and plants (Lakshmanan et al., *Plant Physiol.* 166:689-700 2014). The interplay between microbial species and plants is further affected by agricultural practices, which can improve or degrade the soil microbiome (Adair et al., *Environ. Microbiol. Rep.* 5:404-413 2013; Carbonetto et al., *PLoS One* 9:e99949 2014; Ikeda et al., *Microbes Environ.* 29:50-59 2014). Fertile or highly productive soils contain a different composition of native microbes than soil that is depleted of nutrients and linked to low crop productivity. Different microbial species are associated closely with plants, on the above ground plant surfaces in the phyllosphere, at the root surface in the soil rhizosphere, or intimately as endophytes. Large-scale DNA analysis of these microbe associations has revealed unexpected phylogenetic complexity (Rincon-Florez et al., *Diversity* 5:581-612 2013; Lakshmanan et al., *Plant Physiol.* 166:689-700 2014). Studies have determined complex microbiomes can be correlated to plant productivity, crop yield, stress tolerance, secondary metabolite accumulation, and disease tolerance (Bhardwaj et al., *Microbial Cell Factories* 13:66-75, 2014; Vacheron et al., *Frontiers Plant Science* 4:1-19 2014). Furthermore, plants can specifically select the microbial mixtures from the local environment and potentially fine-tune the microbiome at the level of crop variety (Hartmann et al., *Plant Soil* 321:235-257 2009; Doornbos et al., *Agron. Sustain. Dev.* 32:227-243 2012; Marasco et al., *PLoS One* 7:e48479 2012; Peiffer et al., *Proc. Natl. Acad. Sci. USA* 110:6548-6553; Bulgarelli et al., *Ann. Rev. Plant Biol.* 64:807-838 2014).

Root-associated microbes can promote plant and root growth by promoting nutrient cycling and acquisition, by direct phytostimulation, by mediating biofertilization, or by offering growth advantage through biocontrol of pathogens. Agriculturally useful populations include plant growth promoting rhizobacteria (PGPR), pathogen-suppressive bacteria, mycorrhizae, nitrogen-fixing cyanobacteria, stress tolerance endophytes, plus microbes with a range of biodegradative capabilities. Microbes involved in nitrogen cycling include the nitrogen-fixing *Azotobacter* and *Bradyrhizobium* genera, nitrogen-fixing cyanobacteria, ammonia-oxidizing bacteria (e.g., the genera *Nitrosomonas* and *Nitrospira*), nitrite-oxidizing genera such as *Nitrospira* and *Nitrobacter*, and heterotrophic-denitrifying bacteria (e.g., *Pseudomonas* and *Azospirillum* genera; Isobe and Ohte, *Microbes Environ.* 29:4-16 2014). Bacteria reported to be active in solubilization and increasing plant access to phosphorus include the *Pseudomonas, Bacillus, Micrococcus,* and *Flavobacterium*, plus a number of fungal genera (Pindi et al., *J. Biofertil. Biopest.* 3:4 2012), while *Bacillus* and *Clostridium* species help solubilize and mobilize potassium (Mohammadi et al., *J. Agric. Biol. Sci.* 7:307-316 2012). Phytostimulation of plant growth and relief of biotic and abiotic stresses is delivered by numerous bacterial and fungal associations, directly through the production of stimulatory secondary metabolites or indirectly by triggering low-level plant defense responses (Gaiero et al., *Amer. J. Bot.* 100:1738-1750 2013; Bhardwaj et al., *Microbial Cell Factories* 13:66-76 2014).

In addition to activity in the environment, microbes can also deliver unique biodegradative properties in vitro, under conditions of directed fermentation. Use of specific microbial mixtures to degrade chitin and total protein can yield new bioactive molecules such as free L-amino acids, L-peptides, chitin, and chitosan known to enhance growth or boost stress tolerance via activation of plant innate immunity (Hill et al., *PLoS One* 6:e19220 2011; Tanaka et al., *Plant Signal Behav.* E22598-147 2013). Specific microbial communities can serve multiple tasks, by delivering unique fermentation breakdown products, which are themselves biologically beneficial to crops, plus the resultant microbial consortium, which can be delivered as an agricultural product to enhance crop productivity.

As described herein, consortia of aerobic and/or anaerobic microbes derived from fertile soil and marine sources have been successfully co-fermented and stabilized, offering direct growth and yield benefits to crops. Enzymatic activity of these microbial mixtures has further yielded fermentation products with chitin, glucosamine, protein, and/or amino acids. In some embodiments, direct delivery of microbial consortia and/or compositions can allow early root colonization and promote rhizosphere or endophytic associations. In some embodiments, benefits of delivery of microbial consortia to plants include one or more of increased root growth, increase root hair production, increased root surface area, stronger plants able to withstand transplantation shock, faster stand establishment, resistance to abiotic stress, and higher plant productivity and yield. Complex microbial mixes can span across plant species and genotypes, interacting with microbial soil communities to offer benefits to a wide range of crops growing under different agricultural conditions.

I. Terms

Unless otherwise noted, technical terms are used according to conventional usage. Definitions of common terms in molecular biology may be found in Krebs et al., *Lewin's Genes XI*, published by Jones and Bartlett Learning, 2012 (ISBN 1449659853); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 2011 (ISBN 8126531789); and George P. Rédei, *Encyclopedic Dictionary of Genetics, Genomics, and Proteomics*, 2nd Edition, 2003 (ISBN: 0-471-26821-6).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." As used herein, "comprises" means "includes." Thus, "comprising A or B," means "including A, B, or A and B," without excluding additional elements. All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

To facilitate review of the various embodiments of this disclosure, the following explanations of specific terms are provided:

Aquatic Animal: An animal that lives in salt or fresh water. In particular embodiments disclosed herein, an aquatic animal includes aquatic arthropods, such as shrimp, krill, copepods, barnacles, crab, lobsters, and crayfish. In other embodiments, an aquatic animal includes fish. An aquatic animal by-product includes any part of an aquatic animal, particularly parts resulting from commercial processing of an aquatic animal. Thus, in some examples, aquatic animal by-products include one or more of shrimp cephalothorax or exoskeleton, crab or lobster exoskeleton, or fish skin or scales.

Contacting: Placement in direct physical association, including both in solid and liquid form. For example, contacting can occur with one or more microbes (such as the microbes in a microbial consortium) and a biological sample in solution. Contacting can also occur with one or more microbes (such as the microbes in a microbial consortium) and soil, plants, and/or plant parts (such as foliage, stem, seedling, roots, and/or seeds).

Culturing: Intentional growth of one or more organisms or cells in the presence of assimilable sources of carbon, nitrogen and mineral salts. In an example, such growth can take place in a solid or semi-solid nutritive medium, or in a liquid medium in which the nutrients are dissolved or suspended. In a further example, the culturing may take place on a surface or by submerged culture. The nutritive medium can be composed of complex nutrients or can be chemically defined.

Fermenting: A process that results in the breakdown of complex organic compounds into simpler compounds, for example by microbial cells (such as bacteria and/or fungi). The fermentation process may occur under aerobic conditions, anaerobic conditions, or both (for example, in a large volume where some portions are aerobic and other portions are anaerobic). In some non-limiting embodiments, fermenting includes the enzymatic and/or non-enzymatic breakdown of compounds present in aquatic animals or animal by-products, such as chitin.

Liquid fertilizer: An aqueous solution or suspension containing soluble nitrogen. In some examples, the soluble nitrogen in a liquid fertilizer includes an organic source of nitrogen such as urea, or urea derived from anhydrous ammonia (such as a solution of urea and ammonium nitrate (UAN)). Aqua ammonia (20-32% anhydrous ammonia) can also be used. In other examples, the soluble nitrogen in a liquid fertilizer includes nitrogen-containing inorganic salts such as ammonium hydroxide, ammonium nitrate, ammonium sulfate, ammonium pyrophosphate, ammonium thiosulfate or combinations of two or more thereof. In some embodiments the liquid fertilizer includes a non-naturally occurring nitrogen source (such as ammonium pyrophosphate or ammonium thiosulfate) and/or other non-naturally occurring components.

Common liquid non-natural fertilizer blends are specified by their content of nitrogen-phosphate-potassium (N—P—K percentages) and include addition of other components, such as sulfur or zinc. Examples of human-made blends include 10-34-0, 10-30-0 with 2% sulfur and 0.25% zinc (chelated), 11-37-0, 12-30-0 with 3% sulfur, 2-4-12, 2-6-12, 4-10-10, 3-18-6, 7-22-5, 8-25-3, 15-15-3, 17-17-0 with 2% sulfur, 18-18-0, 18-18-0 with 2% sulfur, 28-0-0 UAN, 9-27-0 with 2% sulfur and potassium thio-sulfate.

Microbe: A microorganism, including but not limited to bacteria, archaebacteria, fungi, and algae (such as microalgae). In some examples, microbes are single-cellular organisms (for example, bacteria, cyanobacteria, some fungi, or some algae). In other examples, the term microbes includes multi-cellular organisms, such as certain fungi or algae (for example, multicellular filamentous fungi or multicellular algae).

Microbial composition: A composition (which can be solid, liquid, or at least partially both) that includes at least one microbe (or a population of at least one microbe). In some examples, a microbial composition is one or more microbes (or one or more populations of microbes) in a liquid medium (such as a storage, culture, or fermentation medium), for example, as a suspension in the liquid medium. In other examples, a microbial composition is one or more microbes (or one or more populations of microbes) on the surface of or embedded in a solid or gelatinous medium (including but not limited to a culture plate), or a slurry or paste.

Microbial consortium: A mixture, association, or assemblage of two or more microbial species, which in some instances are in physical contact with one another. The microbes in a consortium may affect one another by direct physical contact or through biochemical interactions, or both. For example, microbes in a consortium may exchange nutrients, metabolites, or gases with one another. Thus, in some examples, at least some of the microbes in a consortium may be metabolically interdependent. Such interdependent interactions may change in character and extent through time and with changing culture conditions.

II. Microbial Consortia and Compositions Disclosed herein are several microbial consortia. An exemplary microbial consortium of the present disclosure was deposited with the American Type Culture Collection (ATCC, Manassas, Va.) on Nov. 25, 2014, and assigned deposit number PTA-121751, referred to herein as A1002. The A1002 consortium includes at least *Bacillus* spp., *Azospirillum* spp., *Pseudomonas* spp., *Lactobacillus* spp., *Desulfococcus* spp., *Desulfotomaculum* spp., *Marinobacter* spp., *Nitrosopumilus* spp. *Ruminococcus* spp., *Aquabacterium* spp., *Acidisoma* spp., *Microcoleus* spp., *Clostridium* spp., *Xenococcus* spp., *Brevibacterium* spp., *Methanosaeta* spp., *Lysinibacillus* spp., and *Paenibacillus* spp., identified by microarray analysis and/or 16S rDNA sequencing. Also disclosed herein are consortia or microbial compositions including two or more (such as 2 or more, 5 or more, 10 or more, 20 or more, or 50 or more) or all of the microbes in A1002. In some embodiments, a microbial composition disclosed herein is a defined composition, for example a composition including specified microbial species and optionally, additional non-microbial components (including but not limited to, salts, trace elements, chitin, chitosan, glucosamine, and/or amino acids).

As discussed below, the identity of microbes present in A1002 was determined using microarray analysis (Example 3) and/or 16S rDNA sequencing (Example 4). Additional techniques for identifying microbes present in a microbial mixture or consortium are known to one of ordinary skill in the art, including sequencing or PCR analysis of nucleic acids, such as 16S rDNA, from individual microbial colonies grown from within the consortium or mixture. Additional techniques for identifying microbes present in a microbial mixture or consortium also include 1) nucleic acid-based methods which are based on the analysis and differentiation of microbial DNA (such as DNA microarray analysis of nucleic acids, metagenomics or in situ hybridization coupled with fluorescent-activated cell sorting (FACS)), 2) biochemical methods which rely on separation and identification of a range biomolecules including fatty acid methyl esters analysis (FAME), Matrix-assisted laser desorption ionization-time of flight (MALDI-TOF) mass spectrometry analysis, or cellular mycolic acid analysis by High Performance Liquid Chromatography (MYCO-LCS) analysis, and 3) microbiological methods which rely on traditional tools (such as selective growth and microscopic examination) to provide more general characteristics of the community as a whole, and/or narrow down and identify only a small subset of the members of that community.

In some examples, microbes in a mixture or consortium are separated (for example using physical size and/or cell sorting techniques) followed by deep DNA or full genome sequencing of the resulting microbes (or subgroups or subpopulations of microbes). Use of a different microarray or use of other identification techniques may identify presence of different microbes (more, fewer, or different microbial taxa or species) than the microarray analysis performed on A1002 described herein, due to differences in sensitivity and specificity of the analysis technique chosen. In addition, various techniques (including microarray analysis or PCR DNA analysis) may not detect particular microbes (even if they are present in a sample), for example if probes capable of detecting particular microbes are not included in the analysis. In addition, one of ordinary skill in the art will recognize that microbial classification and naming may change over time and result in reclassification and/or renaming of microbes.

In other embodiments the disclosed microbial consortia or compositions include, consist essentially of, or consist of 2 or more (such as 5 or more, 10 or more, 15 or more, 20 or more, or all) of the microbes listed in Table 1.

TABLE 1

Microbes

| Microbe | Exemplary species |
| --- | --- |
| Desulfococcus spp. | |
| Desulfotomaculum spp. | |
| Marinobacter spp. | Marinobacter bryozoorum |
| Nitrosopumilus spp. | |
| Azospirillum spp. | |
| Bacillus spp. | Bacillus subtilis, Bacillus cereus, Bacillus megaterium, Bacillus licheniformis, Bacillus thuringiensis ,Bacillus amyloliquefaciens, Bacillus pasteurii, Bacillus oleronius |
| Lactobacillus spp. | Lactobacillus acidophilus, Lactobacillus casei, Lactobacillus brevis, Lactobacillus paracasei, Lactobacillus delbrueckii, Lactobacillus buchneri |
| Ruminococcus spp. | Ruminococcus flavefaciens |
| Aquabacterium spp. | |
| Acidisoma spp. | |
| Microcoleus spp. | |
| Pseudomonas spp. | Pseudomonas fluorescens |
| Clostridium spp. | Clostridium butyricum, Clostridium pasteurianum, Clostridium beijerinckii, Clostridium sphenoides, Clostridium bifermentans |
| Xenococcus spp. | |
| Brevibacterium spp. | |
| Methanosaeta spp. | |
| Lysinibacillus spp. | Lysinibacillus sphaericus |
| Paenibacillus spp. | Paenibacillus chibensis |

The consortia or compositions can optionally include one or more additional microbes. Additional microbes include, but are not limited to one or more of Deinococcus spp., Leptolyngbya spp., Azotobacter spp. (e.g., Azotobacter vinelandii), Bradyrhizobium spp., Leptospirillum spp. (e.g., Leptospirillum ferrodiazotroph), Paenibacillus spp. (e.g., Paenibacillus amyloticus), Rhodoferax spp., Halorhabdus spp., Rhizobium spp. (e.g., Rhizobium japonicum), Bradyrhizobium spp., Micrococcus spp. (e.g., micrococcus luteus), Nitrobacter spp., Nitrosomonas spp., Nitrococcus spp., Cytophaga spp., Actinomyces spp., Devosia spp., Streptomyces spp., Streptococcus spp., Lactococcus spp., Proteus spp. (e.g., Proteus vulgaris), Trichoderma spp. (e.g., Trichoderma harzianum), Pediococcus spp. (e.g., Pediococcus pentosaceus), Acetobacter spp. (e.g., Acetobacter aceti), Treponema spp., Candidatus spp., Saccharomyces spp. (e.g., Saccharomyces cerevisiae), Penicillium (e.g., Penicillium roqueforti), Monascus (e.g., Monascus ruber), Aspergillus spp. (e.g., Aspergillus oryzae), Arthrospira (e.g., Arthrospira platensis), and Ascophyllum spp. (e.g., Ascophyllum nodosum). Suitable additional microbes can be identified by one of skill in the art, for example, based on characteristics desired to be included in the consortia or compositions.

The disclosed microbial consortia or compositions may include one or more further components in addition to the microbes, including by not limited to salts, metal ions, and/or buffers (for example, one or more of $KH_2PO_4$, $K_2HPO_4$, $CaCl_2$, $MgSO_4$, $FeC_{13}$, $NaMoO_4$, and/or $Na_2MoO_4$), trace elements (such as sulfur, sulfate, sulfite, copper, or selenium), vitamins (such as B vitamins or vitamin K), sugars (such as sucrose, glucose, or fructose), chitin, chitosan, glucosamine, protein, and/or amino acids. Additional components that may also be included in the compositions include HYTb, HYTc, and/or HYTd, one or more fertilizers (e.g., liquid fertilizer), one or more pesticides, one or more fungicides, one or more herbicides, one or more insecticides, one or more plant hormones, one or more plant elicitors, or combinations of two or more of these components.

In some embodiments, the microbial consortia, or a composition including five or more microbial species in the microbial consortia described herein are in a liquid medium (such as a culture or fermentation medium) or inoculum. In other embodiments, the microbial consortia or composition including five or more microbial species listed in Table 1 are present on a solid or gelatinous medium (such as a culture plate) containing or supporting the microbes.

In yet other embodiments, the microbial consortia or composition including five or more microbial species are present in a dry formulations, such as a dry powder, pellet, or granule. Dry formulations can be prepared by adding an osmoprotectant (such as a sugar, for example, trehalose and/or maltodextrin) to a microbial composition in solution at a desired ratio. This solution is combined with dry carrier or absorptive agent, such as wood flour or clay, at the desired concentration of microbial composition (such as 2-30%, for example, 2.5-10%, 5-15%, 7.5-20%, or 15-30%). Granules can be created by incorporating clay or polymer binders that serve to hold the granules together or offer specific physical or degradation properties. Granules can be formed using rotary granulation, mixer granulation, or extrusion, as a few possible methods. Additional methods for preparing dry formulations including one or more microbial species are known to one of ordinary skill in the art, for example as described in *Formulation of Microbial Biopesticides: Beneficial Microorganisms, Nematodes and Seed Treatments,*

Burges, ed., Springer Science, 1998; Bashan, *Biotechnol. Adv.* 16:729-770, 1998; Ratul et al., *Int. Res. J. Pharm.* 4:90-95, 2013.

In some examples, compositions including the microbes or microbial consortia may be maintained at a temperature supporting growth of the microbe(s), for example at about 25-45° C. (such as about 30-35° C., about 30-40° C., or about 35-40° C.). In other examples, the compositions are stored at temperatures at which the microbe(s) are not growing or are inactive, such as less than 25° C. (for example, 4° C., −20° C., −40° C., −70° C., or below). One of skill in the art can formulate the compositions for cold storage, for example by including stabilizers (such as glycerol). In still further examples, the compositions are stored at ambient temperatures, such as about 0-35° C. (for examples, about 10-30° C. or about 15-25° C.).

III. Biodegradation Processes

Figure 2:
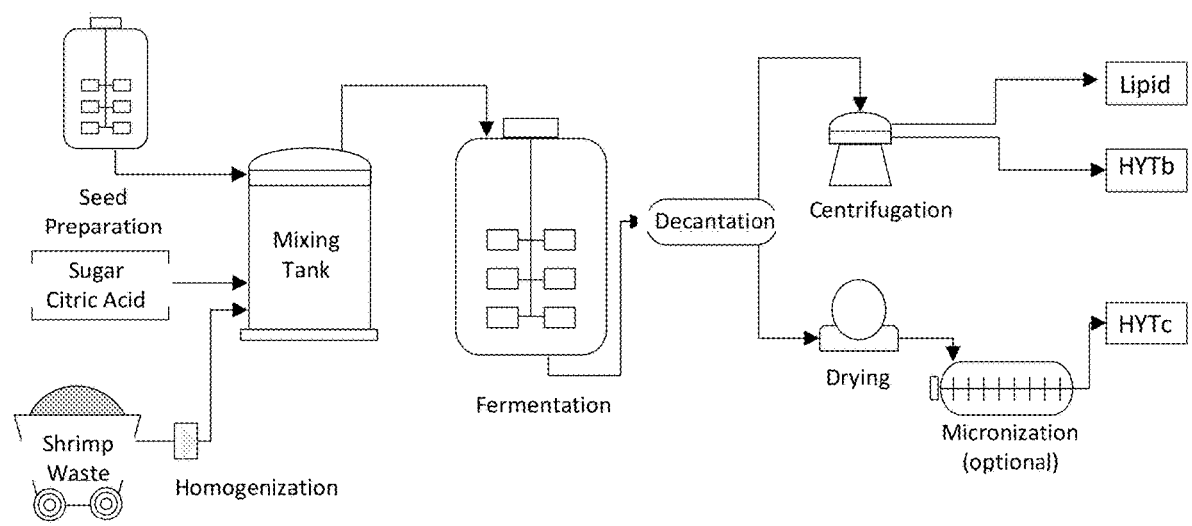
FIG. 2 is a schematic showing an exemplary process for biodegradation of a chitin-containing biological material (exemplified as shrimp waste) with a disclosed microbial consortium or microbial composition.
Figure 3:
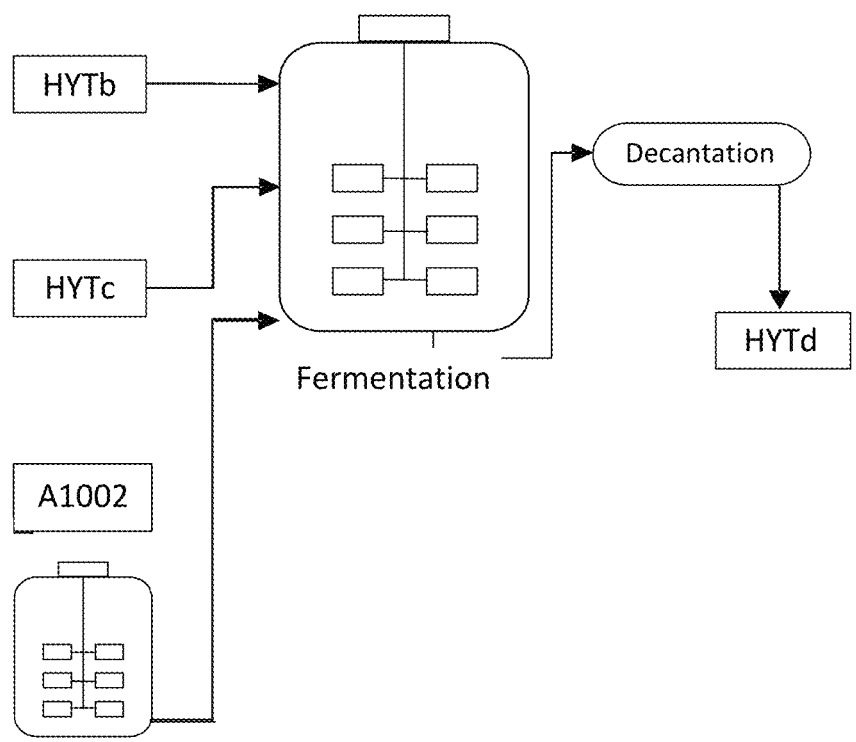
FIG. 3 is a schematic showing an exemplary process for biodegradation of chitin with a disclosed microbial consortium or microbial composition (such as A1002).

The disclosed microbial consortia or compositions can be used to degrade biological materials, such as chitin-rich materials, for example, aquatic animals or aquatic animal by-products, insects, or fungi. Thus, in some embodiments, disclosed herein are methods including mixing one or more of the disclosed microbial consortia or compositions with a chitin-containing biological material to form a mixture, and fermenting the mixture. In some embodiments, the methods also include separating the mixture into solid, aqueous, and optionally, lipid fractions (FIG. 2).

In some embodiments, a biodegradation process disclosed herein includes mixing a microbial consortium (such as A1002, a composition including some or all of the microbes in A1002, or a composition including five or more of the microbial species in Table 1) with one or more chitin-containing biological materials. Chitin-containing biological materials include, but are not limited to, aquatic animals or aquatic animal by-products, insects, or fungi. In some examples, the chitin-containing biological material is an aquatic animal, such as an aquatic arthropod (for example, a member of Class Malacostraca). Aquatic arthropods for use in the disclosed methods include shrimp, crab, lobster, crayfish, or hill. In some examples, the entire aquatic animal (such as an aquatic arthropod) or aquatic animal by-products are used in the biodegradation methods disclosed herein. Aquatic animal by-products include any part of an aquatic animal, such as any part produced by processing of the aquatic animal. In some examples, an aquatic animal by-product is all or a portion of an aquatic animal exoskeleton, such as shrimp, crab, crayfish, or lobster shell. In other examples, an aquatic animal by-product is a part of an aquatic animal, for example, shrimp cephalothoraxes.

In other examples, the chitin-containing biological material includes fungi, such as fungi from Phylum Zygomycota, Basidiomycota, Ascomycota, or Deuteromycota. Particular exemplary fungi include *Aspergillus* spp., *Penicillium* spp., *Trichoderma* spp., *Saccharomyces* spp., and *Schizosaccharomyces* spp. Thus, baker, brewer, and distiller waste streams can provide sources for chitin-containing biological material. In still further examples, the chitin-containing biological material includes insects that contain chitin in their exoskeletons, such as grasshoppers, crickets, beetles, and other insects. Byproducts of the processing of such insects are also contemplated to be sources of chitin.

The chitin-containing biological material is mixed with a composition including the microbes described in Section II above (such as the microbial consortium A1002 or other consortium or composition described in Section II) to form a substantially homogeneous mixture. In some examples, the chitin-containing biological material is ground, crushed, minced, milled, or otherwise dispersed prior to mixing with the microbes or microbial consortia described herein. In particular examples, the mixture contains about 10-50% (such as about 10-20%, about 20-30%, about 30-40%, about 25-40%, for example about 25%, about 30%, about 35%, about 40%, about 45%, or about 50%) chitin-containing material (such as shrimp heads) (w/v) in inoculum containing about 0.1-5% (such as about 0.1-1%, about 0.5-2%, about 1-2%, about 2-3%, about 0.1%, about 0.2%, about 0.3%, about 0.5%, about 0.8%, about 1%, about 1.25%, about 1.5%, about 1.75%, about 2%, about 2.5%, about 3%, about 4%, or about 5%) microbes (v/v).

In some examples, the inoculum, chitin-containing biological material, and a sugar (or other carbon source) are mixed together, for example by stirring or agitation. In other examples, one or more of the microbes in the microbial composition or consortium is optionally activated prior to mixing with the chitin-containing biological material and fermentation. Activation is not required for the methods disclosed herein. Adjustments to the time and/or temperature of the fermentation can be made by one of skill in the art, depending on whether the microbes are activated prior to fermentation. Activation of the microbial composition can be by incubating an inoculum of the microbes with a carbon source (such as a sugar, for example, glucose, sucrose, fructose, or other sugar) at a temperature and for a sufficient period of time for the microbes to grow. In some examples, an inoculum of the microbes (such as a microbial consortium or composition described herein) has a concentration of about 0.05-5% v/v (for example, about 0.5-5%, about 0.5-2%, about 1-2%, or about 2-3%) in a liquid medium. The inoculum is diluted in a solution containing about 0.1-1% sugar (for example, about 0.1-0.5%, about 0.1-0.3%, about 0.2-0.6%, or about 0.5-1%, such as about 0.1%, about 0.2%, about 0.3%, about 0.4%, about 0.5%, about 0.6%, about 0.7%, about 0.8%, about 0.9%, or about 1%) and incubated at ambient temperatures, for example about 20-40° C. (such as about 20° C., about 25° C., about 30° C., about 35° C., or about 40° C.) for about 1-5 days (such as about 24 hours, about 48 hours, about 72 hours, about 96 hours, or about 120 hours). In other examples, activation of the microbial composition can be activated by incubating an inoculum of the microbes at a temperature and for a sufficient period of time for the microbes to grow, for example, incubation at about 20-40° C. (such as about 25-35° C.) for 12 hours to 5 days (such as 1-4 days or 2-3 days). In some non-limiting examples, the microbes are considered to be activated when the culture reaches an optical density of >0.005 at 600 nm.

After mixing of the chitin-containing biological material and the microbes or microbial consortium (which are optionally activated), the mixture is fermented. In some examples, the pH of the mixture is measured prior to fermentation. The pH is adjusted to a selected range (e.g., pH about 3 to about 4 or about 3.5 to 4), if necessary, prior to fermentation. The mixture is incubated at a temperature of about 20-40° C. (for example, about 30°-36° C., such as about 30° C., about 31° C., about 32° C., about 33° C., about 34° C., about 35° C., about 36° C., about 37° C., about 38° C., about 39° C., or about 40° C.) for about 1-30 days (such as about 3-28 days, about 7-21 days, about 3, 5, 7, 10, 14, 16, 20, 24, 28, or 30 days). The mixture is agitated periodically (for example, non-continuous agitation). In some examples, the mixture is agitated for a period of time every 1-7 days, for example every 1, 2, 3, 4, 5, 6, or 7 days. In some non-limiting examples, the fermentation proceeds until the titratable acidity (TTA) is about 3-5% and the pH is about 4-5.

Following the fermentation, the resulting fermented mixture is separated into at least solid and liquid fractions. In some examples, the fermentation is passed from the tank to settling equipment. The liquid is subsequently decanted and centrifuged. In one non-limiting example, the fermented mixture is centrifuged at 1250 rpm (930×g) for 15 minutes at about 5° C. to obtain liquid and lipid (e.g., pigment) fractions. The liquid (or aqueous) fraction obtained from the biodegradation process can be stored at ambient temperature. In some non-limiting examples, a sugar is added to the liquid fraction, for example at 1-10% v/v.

The liquid fraction may include components such as protein, amino acids, glucosamine, trace elements (such as calcium, magnesium, zinc, copper, iron, and/or manganese), and/or enzymes (such as lactic enzymes, proteases, lipases, and/or chitinases). In some non-limiting examples, the liquid fraction contains (w/v) about 1-5% total amino acids, about 3-7% protein, about 0.1-2% nitrogen, less than about 0.2% phosphorus, about 0.5-1% potassium, about 4-8% carbon, about 0.2-1% calcium, less than about 0.2% magnesium, less than about 0.2% sodium, and/or about 0.1-0.4% sulfur. In additional non-limiting examples, the liquid fraction includes about 0.01-0.2% glucosamine (for example, about 0.1% or less). The liquid fraction also may contain one or more microbes (e.g., from the inoculum used to start the fermentation process) and/or trace amounts of chitosan or chitin. The liquid fraction is in some examples referred to herein as "HYTb."

The solid fraction obtained from the biodegradation process contains chitin (for example, about 50-70% or about 50-60% chitin). The solid fraction may also contain one or more of trace elements (such as calcium, magnesium, zinc, copper, iron, and/or manganese), protein or amino acids, and/or one or more microbes from the inoculum used to start the fermentation process. The solid fraction is in some examples referred to herein as "HYTc." HYTc is optionally micronized to form micronized chitin and residual chitin. In some non-limiting examples, the solid fraction contains (w/v) about 9-35% total amino acids, about 30-50% crude protein, about 5-10% nitrogen, about 0.3-1% phosphorus, less than about 0.3% potassium, about 35-55% carbon, about 0.5-2% calcium, less than about 0.1% magnesium, about 0.1-0.4% sodium, and/or about 0.2-0.5% sulfur.

In some examples, a lipid fraction is also separated from the solid and liquid fractions. The lipid fraction is the upper phase of the liquid fraction. The lipid fraction contains compounds such as sterols, vitamin A and/or vitamin E, fatty acids (such as DHA and/or EHA), and in some examples, carotenoid pigments (for example, astaxanthin). The lipid fraction may be used for a variety of purposes, including but not limited to production of cosmetics or nutritional products.

In additional embodiments, chitin is fermented with a microbial consortium (such as A1002 or some or all of the microbes in A1002) or a composition containing five or more of the microbial species in Table 1. In some examples chitin (such as HYTc, or micronized and/or residual chitin produced as described above) is mixed with a microbial consortium or composition containing microbes described herein and protein hydrolyzate (e.g., HYTb), and fermented to form a fermented mixture. At least a portion of the chitin in the starting mixture is digested as a result of the fermentation. In some examples, the mixture is incubated at a temperature of about 20-40° C. (for example, about 30°-35° C., such as about 30° C., about 31° C., about 32° C., about 33° C., about 34° C., about 35° C., about 36° C., about 37° C., about 38° C., about 39° C., or about 40° C.) for about 1 day to 30 days (such as about 2-28 days, about 4-24 days, about 16-30 days, about 10-20 days, or about 12-24 days). In some examples, the mixture is agitated periodically (for example, non-continuous agitation). In other examples, the mixture is continuously agitated. In one non-limiting example, the mixture is agitated for about 1-12 hours daily (such as about 2-8 hours or about 4-10 hours). The pH of the fermentation mixture may be monitored periodically. In some examples, the pH is optionally maintained at about 4-5. In some examples, the fermentation proceeds until Total Titratable Acidity (TTA) is at least about 1-10% (such as about 2-8%, about 4-8%, or about 5-10%).

Following the fermentation, the resulting fermented mixture is separated into at least solid and liquid fractions, for example by decanting, filtration, and/or centrifugation. The liquid fraction resulting from fermentation of HYTb and chitin with the microbial composition is in some examples referred to herein as "HYTd." In some non-limiting examples, the liquid fraction contains (w/v) about 0.5-2% total amino acids, about 3-7% protein, about 0.5-1% nitrogen, less than about 0.1% phosphorus, about 0.4-1% potassium, about 3-7% carbon, less than about 0.5% calcium, less than about 0.1% magnesium, less than about 0.3% sodium, and/or about less than about 0.3% sulfur. In addition, HYTd contains less than about 50% chitin (such as less than about 45%, less than about 40%, less than about 35%, or less than about 30% chitin) and less than 2% glucosamine (such as less than about 1.5% or less than about 1% glucosamine). In other examples, HYTd contains about 25-50% chitin and about 0.5-2% glucosamine.

IV. Processes for Treating Soil, Plants, and/or Seeds

The disclosed microbial consortia, compositions containing microbes, and/or products disclosed herein (such as HYTb, HYTc, and/or HYTd) can be used to treat soil, plants, or plant parts (such as roots, stems, foliage, seeds, or seedlings). In some examples, treatment with the microbial consortia, compositions containing microbes, and/or products improve plant growth, improve stress tolerance, and/or increase crop yield.

In some embodiments the methods include contacting soil, plants (such as plant foliage, stems, roots, seedlings, or other plant parts), or seeds with a consortium (such as A1002) or a composition including the microbes present in one or more of the disclosed microbial consortia or compositions. The methods may also include growing the treated plants, plant parts, or seeds and/or cultivating plants, plant parts, or seeds in the treated soil.

The microbes are optionally activated before application. In some examples, activation of the microbes is as described in Section III, above. In other examples, the microbes are activated by mixing 100 parts water and 1 part microbial consortium or composition and incubating at about 15-40° C. (such as about 20-40° C., about 15-30° C., or about 25-35° C.) for about 12 hours-14 days (such as about 1-14 days, 3-10 days, 3-5 days, or 5-7 days). The activation mixture optionally can also include 1 part HYTb, if the microbial consortium or composition is to be applied in combination with HYTb.

In other embodiments, the methods include contacting soil, plants (or plant parts), or seeds with a product of the disclosed microbial consortia or compositions, such as HYTb, HYTc, HYTd, or combinations thereof. In still further embodiments, the methods include contacting soil, plants, or seeds with a disclosed microbial consortium or composition including the disclosed microbes and one or more of HYTb, HYTc, and HYTd (such as one, two, or all of HYTb, HYTc, and HYTd). HYTb, HYTc, and/or HYTd may be separately applied to the soil, plants (or plant parts), and/or seeds, for example sequentially, simultaneously, or substantially simultaneously with the disclosed microbial consortia or compositions containing microbes.

In some examples, the methods further include contacting the soil, plants (or plant part), or seeds with one or more additional components including but not limited to chitin, chitosan, glucosamine, protein, amino acids, liquid fertilizer, one or more pesticides, one or more fungicides, one or more herbicides, one or more insecticides, one or more plant hormones, one or more plant elicitors, or combinations of two or more thereof. The additional components may be included in the composition including the microbes or in the microbial consortia disclosed herein, or may be separately applied to the soil, plants (or plant parts), and/or seeds, for example sequentially, simultaneously, or substantially simultaneously with the disclosed microbial consortia or compositions containing microbes.

In particular embodiments, a microbial consortium or composition is combined with a liquid fertilizer (for example an aqueous solution or suspension containing soluble nitrogen). In some examples, the liquid fertilizer includes an organic source of nitrogen such as urea, or a nitrogen-containing inorganic salt such as ammonium hydroxide, ammonium nitrate, ammonium sulfate, ammonium pyrophosphate, ammonium thiosulfate or combinations thereof. Aqua ammonia (20-24.6% anhydrous ammonia) can also be used as the soluble nitrogen. In some examples, the microbial consortium or composition is combined with the liquid fertilizer (for example, mixed with the liquid fertilizer) immediately before use or a short time before use (such as within 10 minutes to 24 hours before use, for example, about 30 minutes, 1 hour, 2 hours, 3 hours, 4 hours, 6 hours, 8 hours, 12 hours, 16 hours, 18 hours, or 24 hours before use). In other examples, the microbial consortium or composition is combined with the liquid fertilizer (for example mixed with the liquid fertilizer) at least 24 hours before use (such as 24 hours to 6 months, for example, at least 36 hours, at least 48 hours, at least 72 hours, at least 96 hours, at least one week, at least two weeks, at least four weeks, at least eight weeks, or at least 12 weeks before use).

In some examples, the amount of the composition(s) to be applied (for example, per acre or hectare) is calculated and the composition is diluted in water (or in some examples, liquid fertilizer) to an amount sufficient to spray or irrigate the area to be treated (if the composition is a liquid, such as microbial consortia or compositions, HYTb, or HYTd). In other examples, the composition can be mixed with diluted herbicides, insecticides, pesticides, or plant growth regulating chemicals. If the composition to be applied is a solid (such as a dry formulation of microbes, HYTc, chitin, glucosamine, chitosan, or amino acids), the solid can be applied directly to the soil, plants, or plant parts or can be suspended or dissolved in water (or other liquid) prior to use. In some examples, HYTc is dried and micronized prior to use.

The disclosed microbial compositions (alone or in combination with other components disclosed herein, such as HYTb, HYTc, and/or HYTd) can be delivered in a variety of ways at different developmental stages of the plant, depending on the cropping situation and agricultural practices. In some examples, a disclosed microbial composition and HYTb are mixed and diluted with liquid fertilizer and applied at the time of seed planting at a rate of 0.5 to 1 to 2 liters each per acre, or alternatively are applied individually. In other examples, a disclosed microbial composition and HYTb are mixed and diluted and applied at seed planting, and also applied to the soil near the roots at multiple times during the plant growth, at a rate of 0.5 to 1 to 2 liters each per acre, or alternatively are applied individually. In still further examples, a disclosed microbial composition and HYTb are diluted and delivered together through drip irrigation at low concentration as seedlings or transplants are being established, delivered in flood irrigation, or dispensed as a diluted mixture with nutrients in overhead or drip irrigation in greenhouses to seedlings or established plants, or alternatively are applied individually. In additional examples, a disclosed microbial composition is added to other soil treatments in the field, such as addition to insecticide treatments, to enable ease-of-use. In other examples, such as greenhouses, a disclosed microbial composition and HYTb are used individually or together, combined with liquid fertilizer (such as fish fertilizer) and other nutrients and injected into overhead water spray irrigation systems or drip irrigation lines over the course of the plant's growth. In one greenhouse example, a disclosed microbial composition and HYTb are used together, for example, diluted and applied during overhead irrigation or fertigation at a rate of 0.25 to 1 liter at seedling germination, followed by 0.25 to 1 liter mid-growth cycle with fertigation, and final 0.25 to 1 liter fertigation 5-10 days end of growth cycle.

In some embodiments, a disclosed microbial composition or consortium and HYTb are applied together or individually (for example sequentially) to promote yield, vigor, typeness, quality, root development, and stress tolerance in crops. In one specific example where the crop is corn, 1 to 2 L/acre microbial composition is added in-furrow with liquid fertilizer at seed planting, or applied as a side dress during fertilization after V3 stage, followed by 0.5 to 2 L/acre of HYTb as a foliar spray after V5 stage, added and diluted with herbicides, foliar pesticides, micronutrients, or fertilizers.

In another specific example where the crop is potato, 1 to 3 L/acre of microbial composition is diluted and used either alone or with 1 to 3 L/acre of HYTb at tuber planting; this can be followed by subsequent soil applications of the microbial composition and HYTb before tuberization, either alone (e.g., sequentially) or together. After plant emergence, potato foliar applications of HYTb at 1 to 2 L/acre can be applied, either diluted alone or mixed with herbicide, foliar pesticide, micronutrient, or fertilizer treatments, and applied during the growing season one time, two times, three times, four times, or more.

In yet another specific example where the crop is cotton, 1 to 2 L/acre of microbial composition is applied in-furrow at planting, as a side dress, or 2×2 (2 inches to side and 2 inches below seed), with or without fertilizer. At first white cotton bloom, foliar treatments of 0.5 to 2 L/acre HYTb can be applied, diluted alone or combined with other nutrient, herbicide, or pesticidal treatments.

In another particular example where the crop is wheat, the microbial composition (1 to 2 L/acre) is applied after winter dormancy (S4 stage) and HYTb applied foliarly (0.5 to 2 L/acre; S4 to S10 stage).

In an example where the crop is sugarcane, one application method uses a disclosed microbial composition and HYTb at 2 to 4 L/acre each, applied to the soil during cane planting or as a side dress, with foliar HYTb applied at 1 to 2 L/acre, mixing with water or fertilizers or micronutrients.

HYTb can be used alone as a foliar treatment in all crops to improve traits such as plant stress tolerance, vegetative vigor, harvest quality and yield. In an example where the crop is corn, HYTb can be applied at ½ to 1 L/acre, one or multiple times, mixing with water or pesticides or herbicides. In another example, HYTb can be used to treat wheat as a foliar spray, mixed with water or pesticides or herbicides, at a rate of ½ to 1 L/acre, applying one or multiple times.

In all crops, HYTc may be added to the soil at a rate of about 0.5-2 kg/acre (such as about 0.5 kg/acre, about 1 kg/acre, about 1.5 kg/acre, or about 2 kg/acre) at the time of crop establishment or planting. In other examples, HYTc is added to a drip irrigation solution of a disclosed microbial composition and HYTb or is added to fertilization applications containing a disclosed microbial composition and HYTb in greenhouses, such as the examples above.

In additional embodiments, HYTd (alone or in combination with the microbes or other components disclosed herein) is used at about 1-20 L/hectare (such as about 1-15 L/hectare, about 3-10 L/hectare, or about 3-5 L/hectare). In other examples, HYTd (alone or in combination with the microbes or other components disclosed herein) is used as a seed treatment to enhance crop yield and performance (for example, about 1-10 L/kg seed, such as about 1-3 L/kg, about 3-5 L/kg, or about 5-10 L/kg). Alternatively, HYTd can be used in the soil (alone or in combination with the microbes or other components disclosed herein) at about 1-3 L/hectare to increase plant growth, for example to help plants remain productive under conditions of stress.

In some examples, treatment of soil, seeds, plants, or plant parts with a composition comprising the microbes in a disclosed microbial consortium increases plant growth (such as overall plant size, amount of foliage, root number, root diameter, root length, production of tillers, fruit production, pollen production, or seed production) by at least about 5% (for example, at least about 10%, at least about 30%, at least about 50%, at least about 75%, at least about 100%, at least about 2-fold, at least about 3-fold, at least about 5-fold, at least about 10-fold, or more). In other examples, the disclosed methods result in increased crop production of about 10-75% (such as about 20-60% or about 30-50%) compared to untreated crops. Other measures of crop performance include quality of fruit, yield, starch or solids content, sugar content or brix, shelf-life of fruit or harvestable product, production of marketable yield or target size, quality of fruit or product, grass tillering and resistance to foot traffic in turf, pollination and fruit set, bloom, flower number, flower lifespan, bloom quality, rooting and root mass, crop resistance to lodging, abiotic stress tolerance to heat, drought, cold and recovery after stress, adaptability to poor soils, level of photosynthesis and greening, and plant health. To determine efficacy of products, controls include the same agronomic practices without addition of microbes, performed in parallel.

The disclosed methods can be used in connection with any crop (for example, for direct crop treatment or for soil treatment prior to or after planting). Exemplary crops include, but are not limited to alfalfa, almond, banana, barley, broccoli, canola, carrots, citrus and orchard tree crops, corn, cotton, cucumber, flowers and ornamentals, garlic, grapes, hops, horticultural plants, leek, melon, oil palm, onion, peanuts and legumes, pineapple, poplar, pine and wood-bearing trees, potato, raspberry, rice, sesame, sorghum, soybean, squash, strawberry, sugarcane, sunflower, tomato, turf and forage grasses, watermelon, wheat, and *eucalyptus*.

The following examples are provided to illustrate certain particular features and/or embodiments. These examples should not be construed to limit the disclosure to the particular features or embodiments described.

Example 1

Microbial Consortium A1002

This example describes production of microbial consortium A1002.

A1002 was produced from a seed batch of microbes that originally were derived from fertile soils and additional microbes (such as *Bacillus* spp.) (see, e.g., U.S. Pat. No. 8,748,124, incorporated herein by reference). The "seed" culture was mixed with a suspension containing 5.5% w/w whey protein and 1.2% w/w yogurt in water ("C vat") and a suspension containing 0.1% w/w *spirulina* and 0.1% w/w kelp extract in water ("A vat"). The A vat and C vat suspensions were each individually prepared 3 days before mixing with the seed culture and incubated at ambient temperature. The seed culture, C vat, and A vat were mixed at a proportion of about 81:9:9. After mixing, a suspension of additional components containing about 70% v/v molasses, 0.5% v/v HYTb, 0.003% w/v Arabic gum, and 0.02% w/v brewer's yeast (*S. cerevisiae*) were mixed with the mixture of the seed culture, C vat, and A vat, and additional water at a ratio of about 16:34:50. The mixture was fermented for about 7 days at ambient temperature (about 19-35° C.). After 7 days, the tanks were aerated for 30 minutes every other day. Additional water was added (about 10% more v/v) and fermentation was continued under the same conditions for about 10 more days. Additional water was added (about 4% more v/v) and fermentation was continued for about 7 more days, at which time samples were collected for analysis and deposit with the ATCC. A1002 was subsequently stored in totes at ambient temperature.

Example 2

Analysis of Microbes in A1002 by Plating

This example describes analysis of microbes present in A1002 by replicate plating under aerobic and anaerobic conditions.

Samples (50 mL) were collected from an aerated tote of A1002 (stirred with a stainless steel mixing paddle at 120 rpm for 8 minutes) using a sanitized handheld siphon drum pump. On day 1, the sample was vortexed (e.g., 60 seconds at 2000 rpm) to ensure even distribution of microbes. In a tube with 9.8 mL sterile water, 0.1 mL of A1002 sample and 0.1 mL of HYTb were added ($10^{-2}$ dilution). The tube was incubated at 35° C. for 72 hours without shaking. After 72 hours (day 3), the tube was briefly vortexed and a series of 10-fold dilutions in sterile water was prepared $10^{-3}$ to $10^{-9}$ dilutions).

Each dilution was plated (100 µL) on a Nutrient Agar plate (for aerobic microorganism culture) and a Standard Methods Agar plate (for anaerobic microorganism culture), with 3 replicates for each. Nutrient Agar plates were cultured at 27° C. for 48 hours. Standard Methods Agar plates were incubated at 35° C. for 72 hours in an anaerobic chamber. After the incubation, for each culture, a dilution that yielded less than 100 colonies was selected. For the selected dilution all of the colonies on each of the replicate plates were counted and CFU/mL calculated. A1002 yielded $4.6 \times 10^7$ CFU/mL under aerobic conditions and $4.0 \times 10^7$ CFU/mL under anaerobic conditions.

Example 3

Analysis of Microbes in A1002 by Microarray

This example describes microarray analysis of microbes present in A1002.

A sample of A1002 was analyzed by Second Genome (South San Francisco, Calif.) using the G3 PhyloChip™ Assay. DNA was isolated from the sample using Power-Soil® DNA isolation kit (Mo Bio Laboratories, Inc., Carlsbad, Calif.) according to the manufacturer's instructions. 16S rRNA was amplified (35 PCR cycles) using Genes were amplified using the degenerate forward primer 27F.1 (AGRGTTTGATCMTGGCTCAG; SEQ ID NO: 1) and the non-degenerate reverse primer 1492R (GGTTACCTTGT-TACGACTT; SEQ ID NO: 2). The amplification products were concentrated using a solid-phase reversible immobilization method and quantified by electrophoresis using an Agilent 2100 Bioanalyzer®. PhyloChip Control Mix™ was added to each amplified product. The amplicons were fragmented, biotin labeled, and hybridized to the PhyloChip™ G3 array, which includes >1.1 million probes targeting about 55,000 individual microbial taxa, with multiple proves per operational taxonomic unit (OTU). The arrays were washed, stained, and scanned using a GeneArray® scanner (GeneChip® Microarray Analysis Suite, Affymetrix).

Approximately 330 billion molecules were assayed and analyzed using Second Genome's PhyloChip processing software. A series of perfect match (PM) and mis-match (MM) probes sets gave off a florescence intensity (FI) which were captured as pixels in an image and collected as an integer value. The software then made adjustments for background florescence and noise estimation and rank-normalized the results. The results were then used as input to empirical probe-set discovery. The empirical OUT tracked by a probe set was then taxonomically annotated against the May 2013 release of Greengenes 16S rRNA gene database (greengenes.1bl.gov) from the combination of 8-mers contained in all probes of the set. The taxa were then identified by the standard taxonomic name or with a hierarchical taxon identifier.

After the taxa were identified for inclusion in analysis, the values used for each taxa-sample were populated in two distinct ways. In the first case, a relative abundance metric was used to rank the abundance of each taxa relative to the others. The second case used a binary metric or presence/absence score to determine whether each taxon was actually in the sample.

The data from the microarray analysis were also used to select microbes for inclusion in the compositions described herein (such as the microbes listed in Table 1 and elsewhere herein). The microbes (taxa, genus, or species) were ranked in order of relative abundance and microbes were selected based on desired characteristics.

Example 4

Analysis of Microbes in A1002 by Sequencing

This example describes exemplary methods for analysis of microbes in A1002 by sequencing 16S rDNA. One skilled in the art will appreciate that methods that deviate from these specific methods can also be used for successful sequencing and analysis of microbes in A1002.

Genomic DNA was extracted from a sample of A1002. 16S rDNA was amplified by PCR and sequenced, for example using MICROSEQ ID microbial identification system (Applied Biosystems/Life Technologies, Grand Island, N.Y.). Sequencing data was analyzed using SHERLOCK DNA software (MIDI Labs, Newark, Del.). Purified isolates were identified and are listed in Table 2. A species level match was assigned if the % generic difference (% GD) between the unknown and the closest match was less than the approximate average % GD between species within that particular genetic family, which is usually 1%. A genus level match was assigned when the sequence did not meet the requirements for a species level match, but still clustered within the branching of a well-defined genus (GD greater that 1% and less than about 3%).

TABLE 2

Microbes identified in A1002 by 16S rDNA sequencing

| Sample | Microbe | Confidence Level | % GD | Base pairs |
|---|---|---|---|---|
| 1a | Bacillus oleronius | Species | 0.37 | 537 |
| 1b | Bacillus thuringiensis | Species | 0.28 | 537 |
| 1c | Lysinibacillus sphaericus | Genus | 1.96 | 536 |
| 2a | Lactobacillus buchneri | Species | 0.18 | 561 |
| 2c | Bacillus oleronius | Species | 0.19 | 537 |
| 2d | Paenibacillus chibensis | Genus | 3.9 | 538 |
| 3a | Lactobacillus buchneri | Species | 0.27 | 561 |
| 4b | Bacillus oleronius | Species | 0.37 | 537 |
| 5a | Lactobacillus buchneri | Species | 0.36 | 561 |

Example 5

Biodegradation of Chitin-Containing Materials

This example describes exemplary methods for biodegradation of chitin-containing biological materials using the microbial consortium A1002. However, one skilled in the art will appreciate that methods that deviate from these specific methods can also be used for successful biodegradation of chitin-containing biological materials.

Shrimp by-products are obtained from shrimp processing plants and transported in closed, chilled containers. After inspection of the raw material quality, the shrimp by-products are homogenized to reduce particle size to about 3-5 mm. Pre-activated A1002 microbial cultures (about 0.2-100 mL/L) and sugar (about 5 g/L) are mixed with the homogenized shrimp by-product (about 50 g/L) and agitated until the mixture is homogeneous. With continuous agitation, the temperature is maintained at ambient temperature (about 19-35° C.) and the pH is adjusted to 3.5-4.0 with citric acid. The mixed ingredients are transferred into a sanitized fermentation tank (25,000 L) and fermented at 30-36° C. for 120 hrs. Agitation is applied for 30 minutes at least two times a day. During the fermentation process, the pH is monitored, and the total titratable acidity (TTA, %) is determined by titration with 0.1 N NaOH. The fermentation is stopped when the TTA is about 3.5% and/or the pH is about 4-5.

The fermented cultures are fed to a continuous decanter. The separated solid layer from the decanting step is subject to centrifugation to remove the lipid layer. The purified liquid (HYTb) is mixed with sugar (such as molasses, 10% v/v), then stored in holding tanks or dispensed to totes. The solid materials from the decanting step are dried with superheated air at 120° C. until their moisture content is below 8%, then ground to 200 mesh. The dried product (HYTc) is packaged in bags or sacks.

Example 6

Biodegradation of Chitin

This example describes exemplary methods for biodegradation of chitin using the microbial consortium A1002. However, one skilled in the art will appreciate that methods that deviate from these specific methods can also be used for successful biodegradation of chitin.

A1002 microbial culture is pre-activated with sugar (about 2.5 g/L) in a 10,000 L tank for three days. The activated inoculum is mixed with protein hydrolysate such as HYTb (about 500 mL/L) and chitin (HYTc e.g., produced as described in Example 5). The mixture is gently mixed for 1 hour to achieve complete homogenization. The mixture is fermented for 20 days at ambient temperature (e.g., about 19-35° C.) with agitation for about 8 hours daily and pH monitoring (pH 4.0-5.0). Samples may be collected periodically, for instance every two days, for quantification of glucosamine and optionally chitosan. After fermentation is complete, the mixture is filtered through a filter that retains particles of 300 mesh, primarily the remaining chitin. The filtrate is retained and bottled after product characterization.

Example 7

Treatment of Field Corn with Microbial Compositions

This example describes a representative method for obtaining increased corn crop yield, using a microbial consortium. One skilled in the art will appreciate that methods that deviate from these specific methods can also be used for increasing crop yield.

Treatment of field corn with a microbial composition prepared similarly to A1002, or with HYTb, showed a strong increase in final harvestable yield. All agronomic practices of fertilization, cultivation, weed control, and pest control, were identical and side-by-side for the microbial composition- or HYTb-treated plots (Test) and control (Check) plots.

Figure 4A:
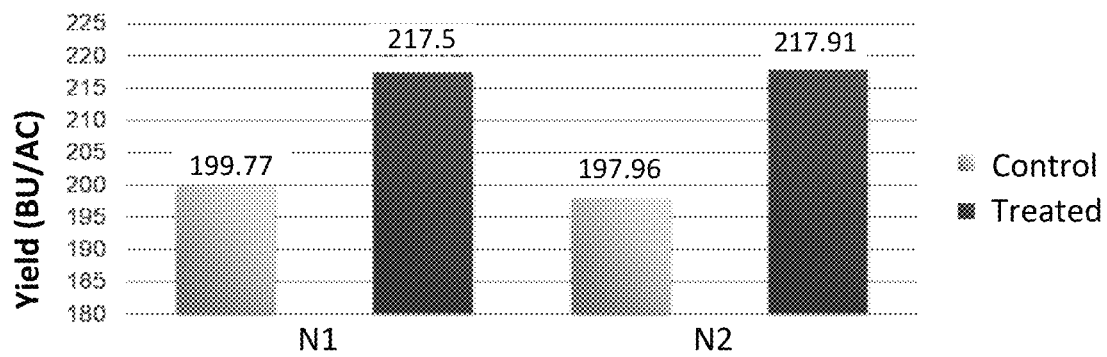
FIGS. 4A-4G are graphs showing the effect on yield of treatment of corn with a microbial composition (FIGS. 4A-4C and 4E), HYTb (FIGS. 4D and 4F), or a microbial composition under water stress conditions (FIG. 4G).

Trial 1 evaluated yield after the microbial composition was added to the typical nitrogen side dress (1 L/acre microbial composition; 32 UAN liquid fertilizer; Test) compared to non-treated control (Check), applied at V2 stage. In two large-scale, replicated strip trials (1 acre total), yield in the Test strips were 8% to 10% higher than parallel control strips (Check) (FIG. 4A).

Figure 4B:
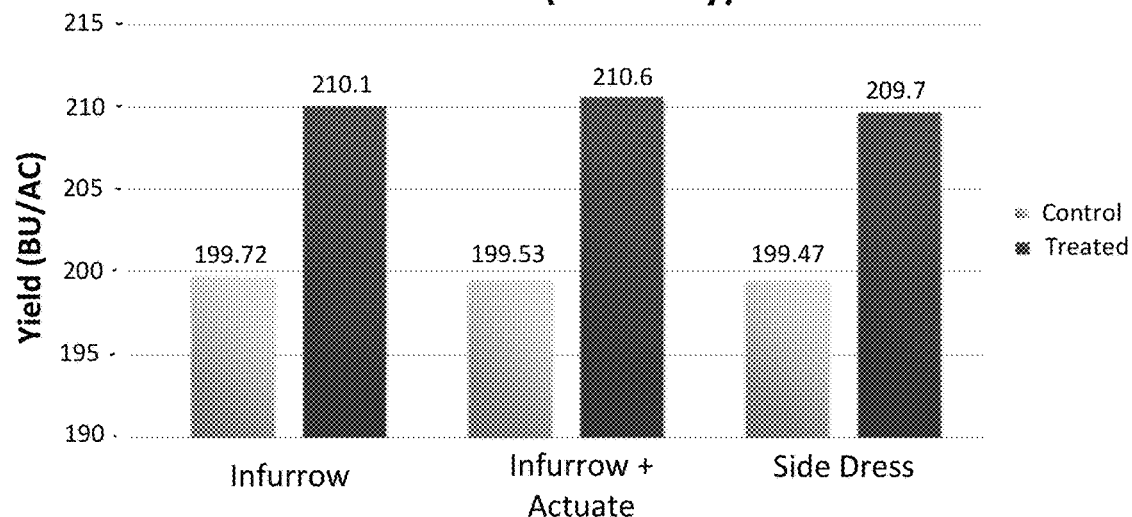

Trial 2 demonstrated that both in-furrow application and addition in the side dress were equally effective for increasing corn yields. In a 1 acre strip trial, large plots were treated with the microbial composition added in-furrow, during seed planting (1 L/acre) or at V2 stage as a side dress (3 gal NPK liquid fertilizer, 1 liter micronutrient mix). Both application methods showed Test strips had about a 5% increase in yield, about 10 Bu/acre compared to controls (FIG. 4B). Adding a commercial blend of 10% humic acid/biostimulant to the Test (Actuate) in-furrow offered the same 5% yield as microbial composition addition alone compared to non-treated control (FIG. 4B).

Figure 4C:
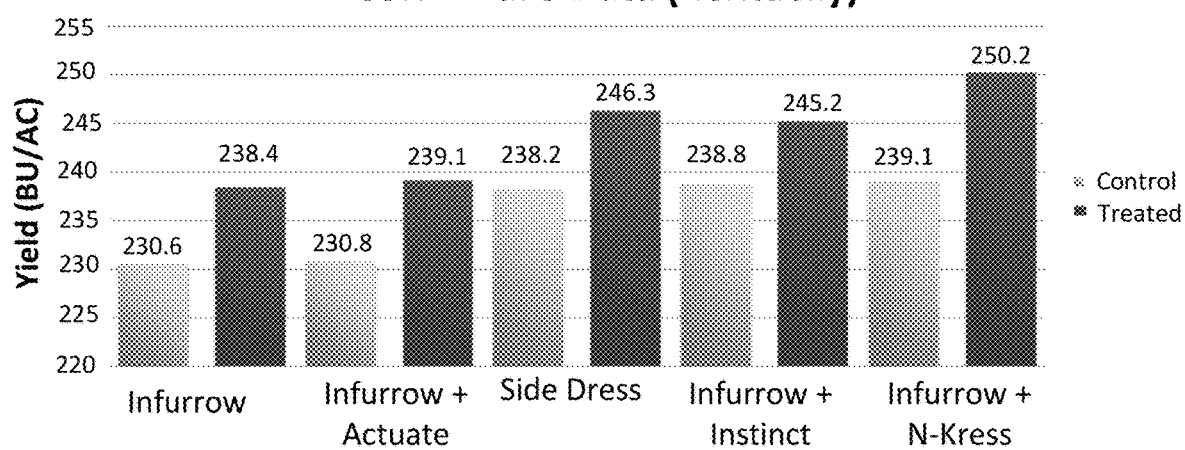

Trial 3 demonstrated that addition of nitrogen-stabilization products either unaffected or slightly boosted the yield enhancing effect of the microbial composition in corn and further validated the consistent boost in yield of the microbial composition delivered either in-furrow or mixed in the side dress (FIG. 4C). In a 1 acre strip trial, both in-furrow and side dress treatments offered a 3% yield boost (8 Bu/acre) over control (Check). Addition of Actuate caused a slight yield increase (4% boost in yield, 9 Bu/acre higher than control). Addition of nitrogen-stabilization products, Instinct or N-Kress, caused either no effect (modest 2.5% yield boost for Instinct) or a slightly higher boost in yield (4.6% yield increase for N-Kress, 11 Bu/acre higher than control).

Figure 4D:
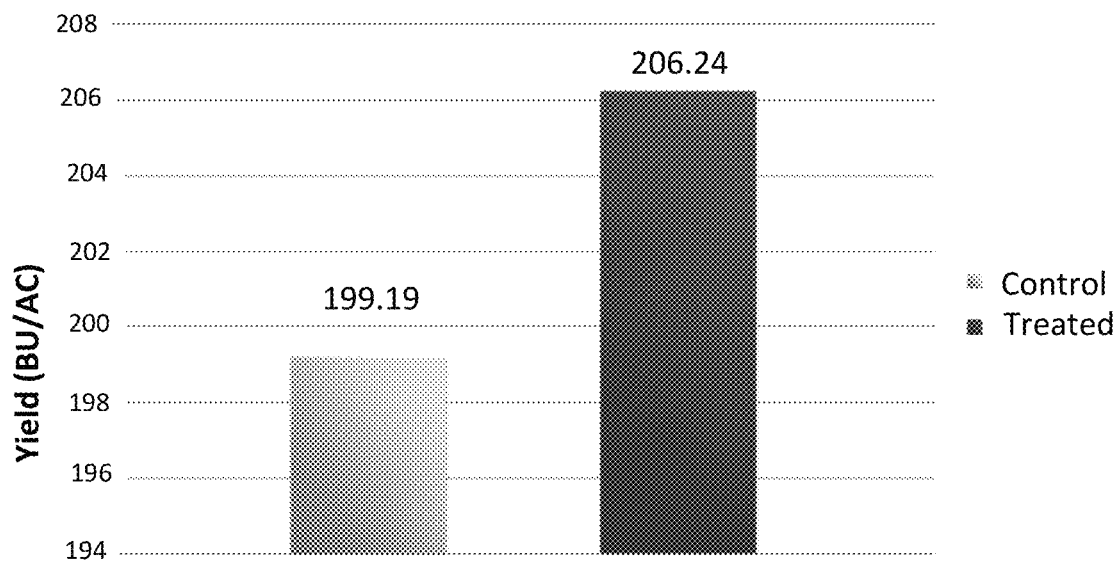

Trial 4 demonstrated that HYTb delivered in-furrow also boosted yield over control plots. In a 20 acre trial, HYTb was added to the in-furrow fertilizer/nutrient mix (1 L/acre). Compared to parallel control acreage (Check), HYTb-treated acres offered a 3.5% (7 Bu/acre) yield increase (FIG. 4D).

Figure 4E:
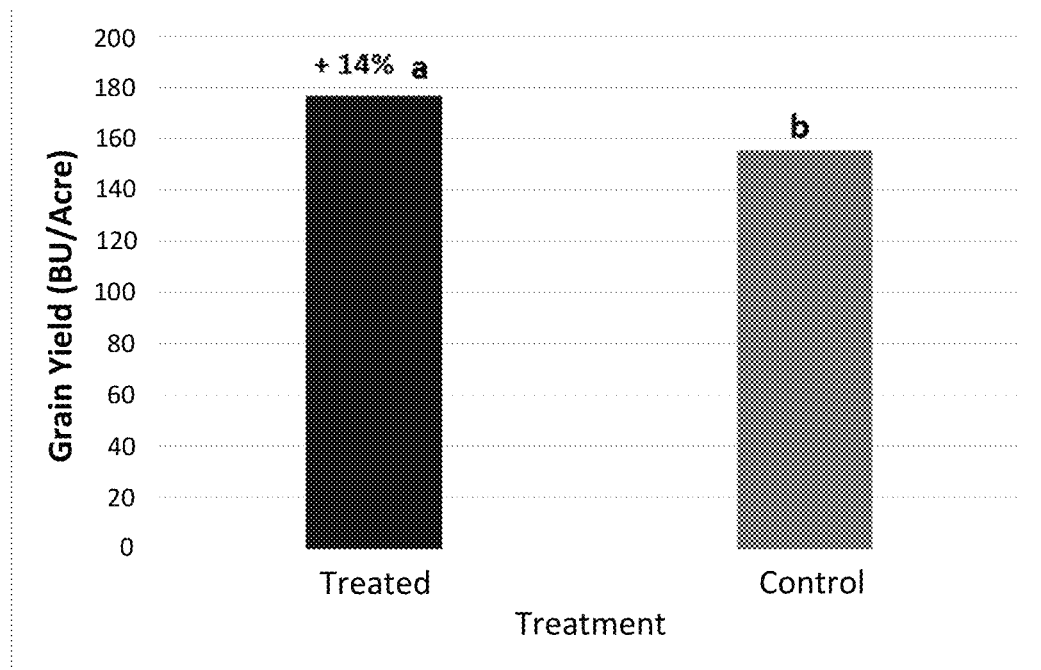

Trial 5 demonstrated that, when evaluated in a replicated plot design trial, a single soil inoculation of corn with the microbial composition at 1 L/acre in furrow at V6 stage, delivered with 28% nitrogen fertilizer via drip irrigation, provided a 14% increase yield over the untreated control across five replicated plots (FIG. 4E).

Figure 4F:
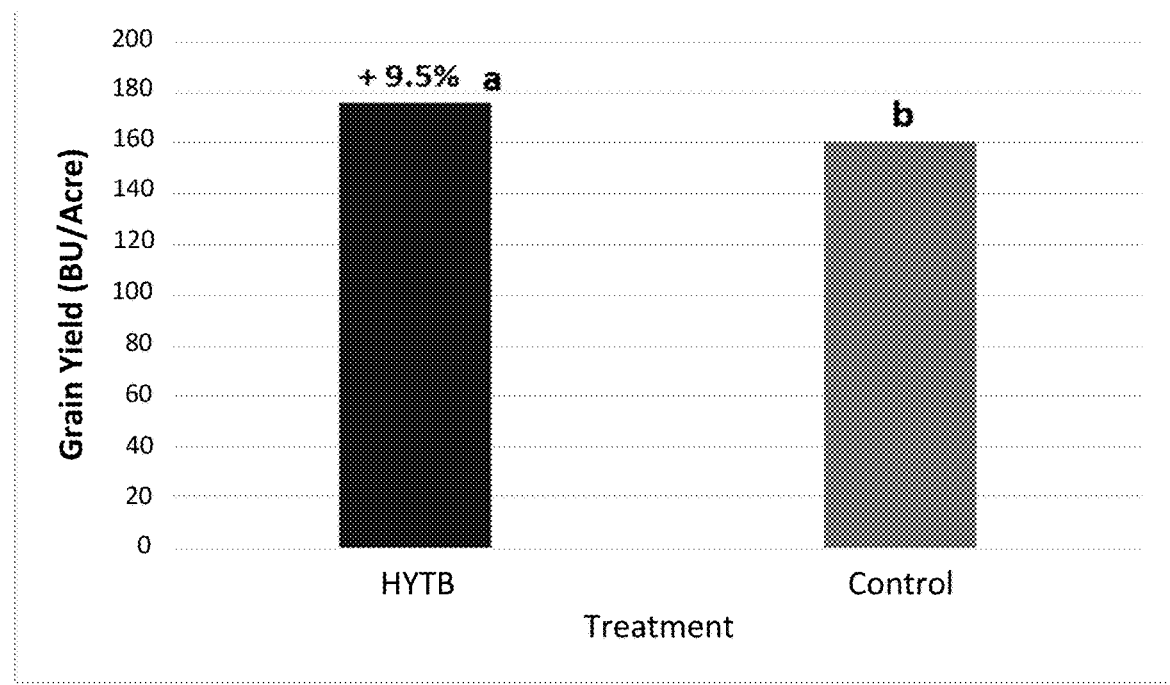

Trial 6 showed that HYTb, when used alone as a foliar treatment in corn, also provided a 9.5% yield increase when compared to the untreated control when tested in a randomized, replicated plot design trial. HYTb was foliar sprayed over two applications of 1 L/acre each application, at the V8 stage and VT stages (FIG. 4F).

Figure 4G:
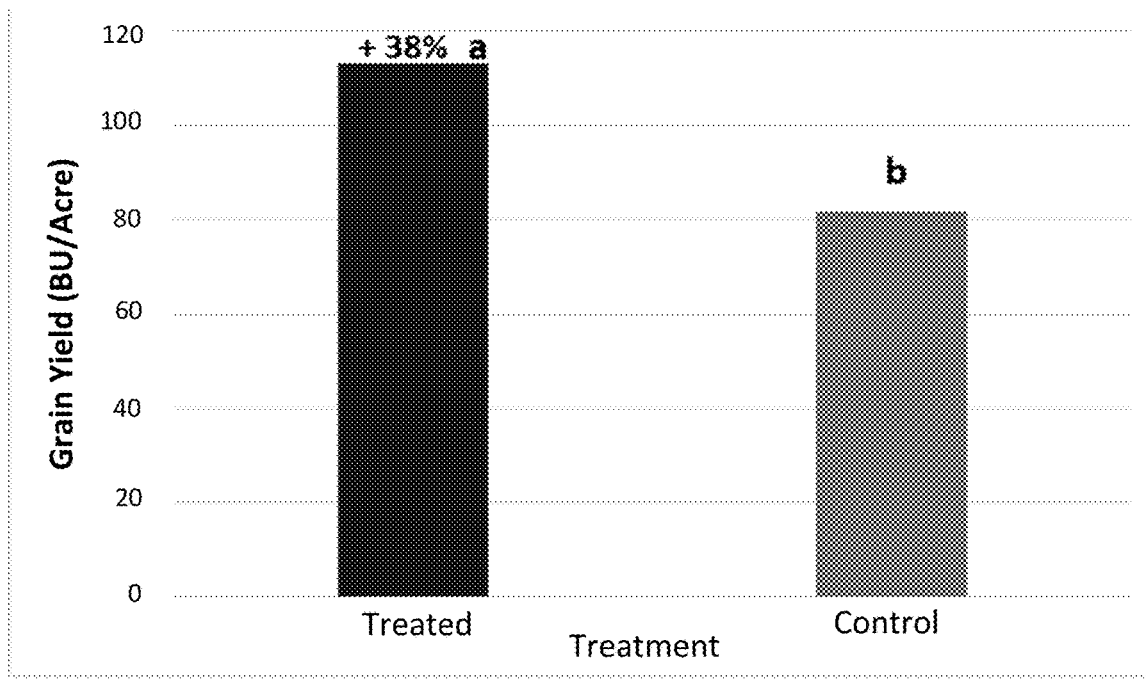

Trial 7 was also a randomized and replicated plot design trial in corn, performed under water stress conditions. In this study, the amount of irrigation was limited to 11 inches of water versus the appropriately watered plots that received 17 inches of irrigation. A single 1 L/acre treatment of microbial composition, delivered at stage V6 with 28% nitrogen fertilizer via drip irrigation (Treated), produced a 38% yield increase over plots treated with fertilizer alone (untreated Check). The harvest increase observed with microbial composition treatment represents a potential of 31 Bu/acre higher yield (FIG. 4G).

Example 8

Treatment of Wheat with Microbial Compositions

This example describes a representative method for obtaining increased wheat crop yield, using a microbial consortium. One skilled in the art will appreciate that methods that deviate from these specific methods can also be used for increasing crop yield.

Treatment of wheat with a microbial composition prepared similarly to A1002, or with HYTb, showed a strong increase in final harvestable yield. All agronomic practices of fertilization, cultivation, weed control, and pest control, were identical and side-by-side for the microbial composition- or HYTb-treated plots (Test) and control (Check) plots.

Figure 5A:
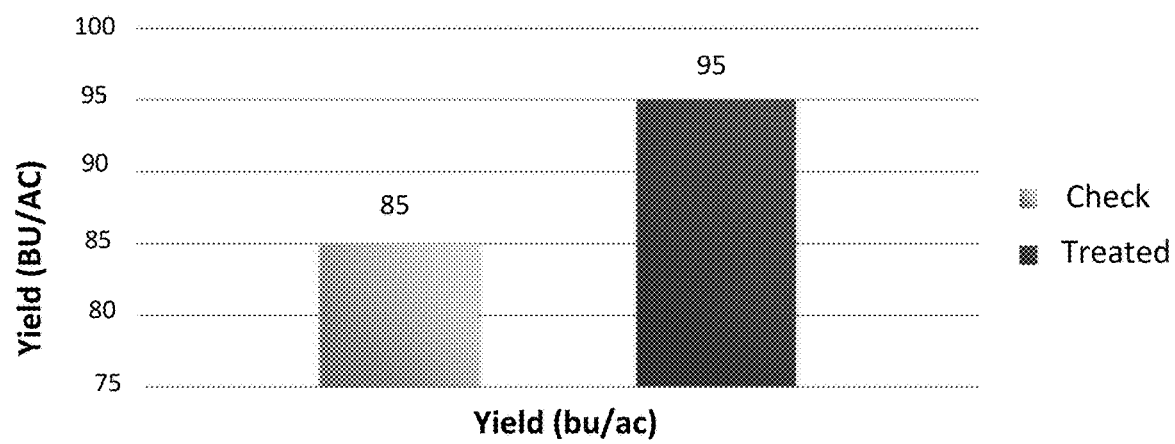
FIGS. 5A-5D show the effect of treatment of wheat with a microbial composition (FIGS. 5A-5B) or with a microbial composition plus HYTb (FIG. 5C) on yield.

Trial 1 showed a strong increase in wheat yield promoted by soil application of the microbial composition. In this 80 acre trial, the microbial composition was added at a rate of 1 L/acre to the top dress fertilizer mix at stage S4. Harvest yields demonstrated an 11% (10 Bu/acre) yield increase with use of the microbial composition (FIG. 5A).

Figure 5B:
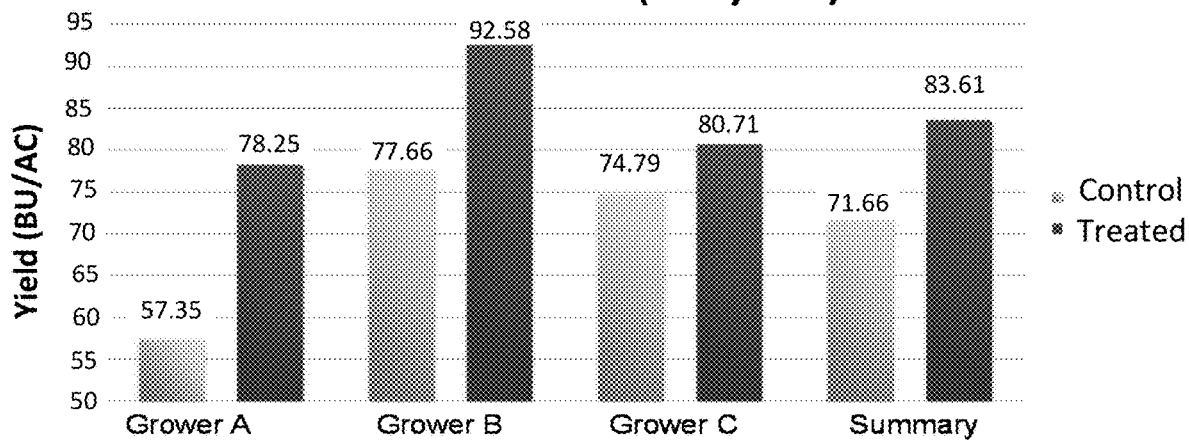

Trial 2 compared three large trials in the same geographic area, totaling 271 acres of microbial composition-treated (test) and 354 acres of parallel untreated wheat (control). All trials were performed the same, with microbial composition (1 L/acre) added to the top dress fertilizer mix and applied at wheat growth stage S4. Relative to parallel control acres on the same farm, the treated wheat gave higher yields, ranging from an increase of 6% to 17% to 36% higher yields, with a three farm average of about 16% increase in yield (FIG. 5B).

Figure 5C:
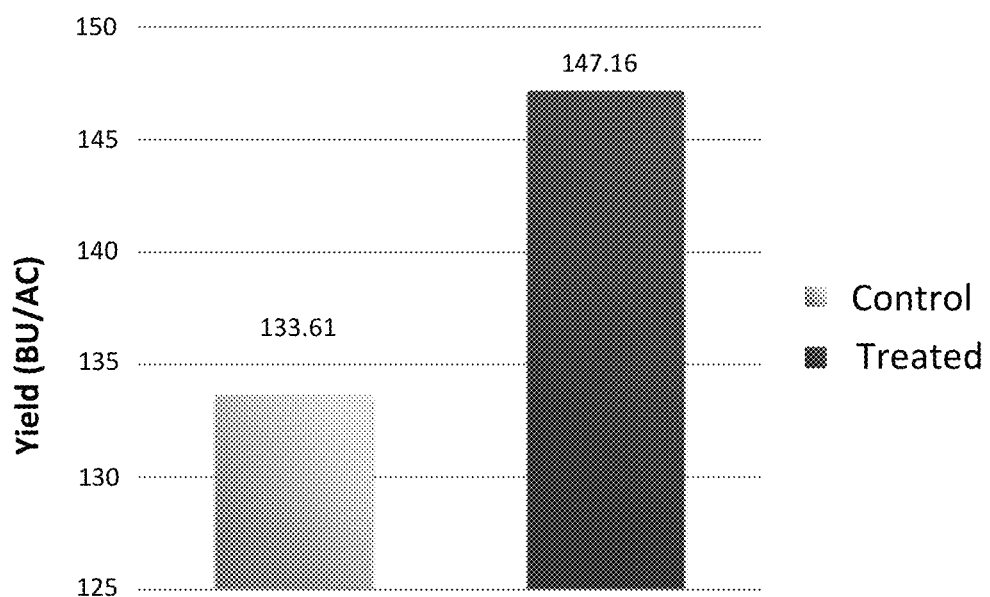
Figure 5D:
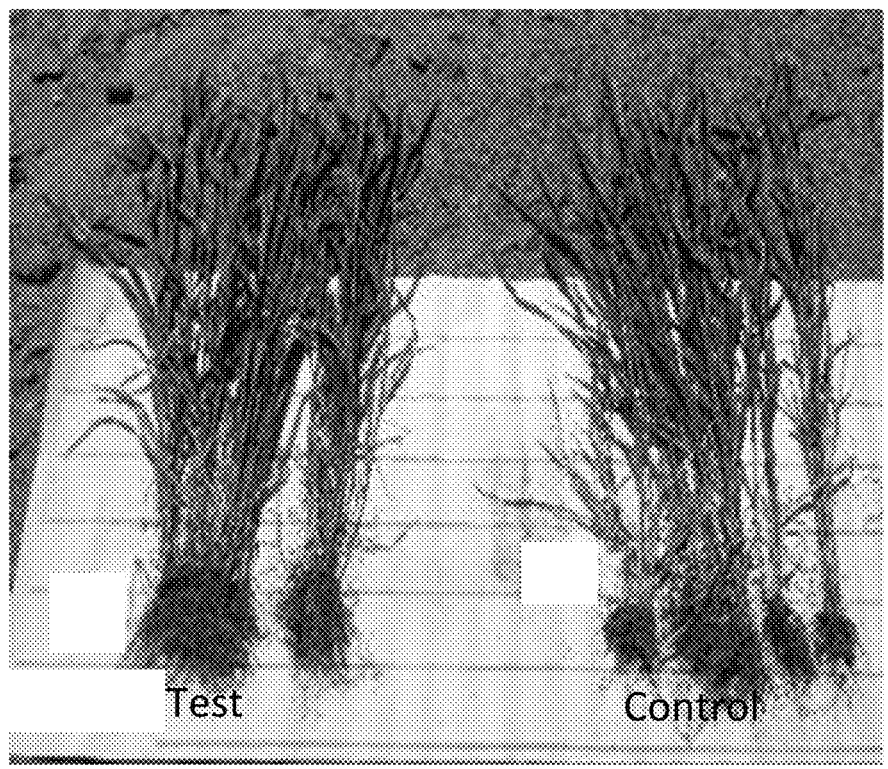

Trial 3 evaluated microbial composition and HYTb treatment of wheat in combination and found that the combination enhanced yield. In a large pivot trial (129 acres), microbial composition was applied pre-plant at a rate of 1 L/acre, incorporated with normal nutritional program, and followed by pivot delivery of HYTb as a foliar spray (1 L/acre) plus herbicide at wheat growth stage S6. Compared to untreated control (Check), the treated acreage gave a 10% higher yield (14 Bu/acre) than control acreage (FIG. 5C). Further, typical wheat plants from the treated plots had visibly more roots than untreated controls (FIG. 5D).

Example 9

Treatment of Tomato with Microbial Compositions

This example describes a representative method for obtaining increased tomato crop yield, using a microbial consortium. One skilled in the art will appreciate that methods that deviate from these specific methods can also be used for increasing crop yield.

Treatment of tomato with a microbial composition prepared similarly to A1002 showed a strong increase in final harvestable yield. All agronomic practices of fertilization, cultivation, weed control, and pest control, were identical and side-by-side for both the microbial composition-treated (Test) and control (Check) plots.

Figure 6A:
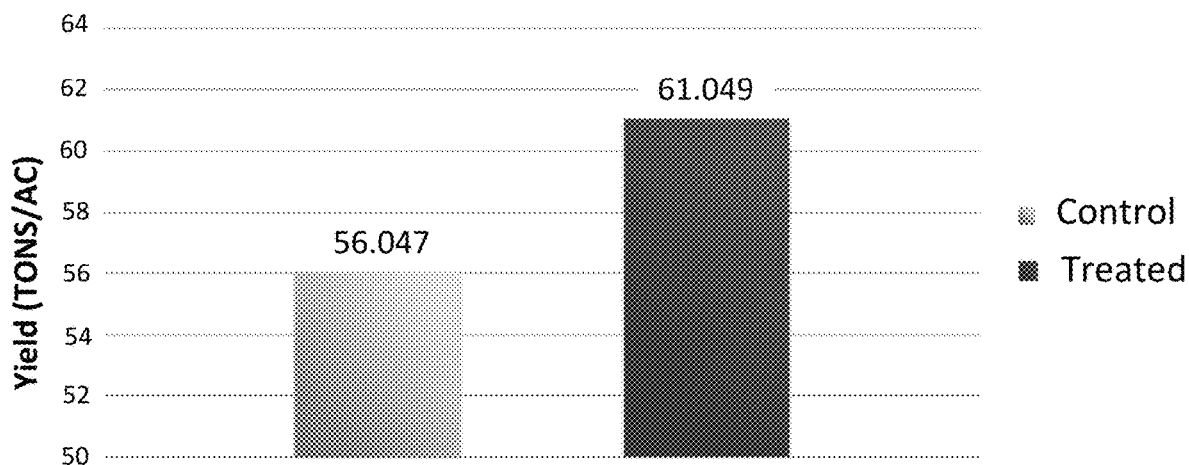

Trial 1 evaluated microbial composition treatment of tomato applied at 1 L/acre with one application at transplant (in transplant water) followed by application by drip irrigation every three weeks (four times). In a 10 acre test plot compared to a 10 acre control plot, the treated acreage gave about 8% higher yield than control (FIG. 6A).

Figure 6B:
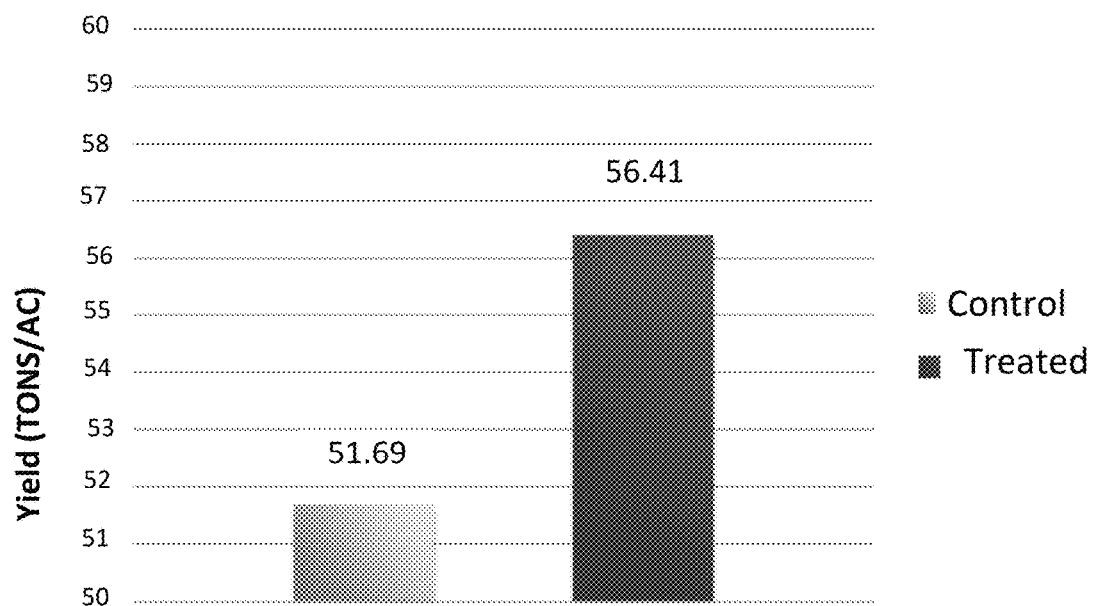

Trial 2 evaluated microbial composition treatment of tomato applied at 1 L/acre by drip irrigation every three weeks (five times). In a 49.6 acre test plot compared to a 4.45 acre control plot, the treated acreage gave about 9% higher yield than control (FIG. 6B).

Trial 3 evaluated microbial composition treatment of tomato applied at 1 L/acre with one application at transplant (in transplant water) followed by application by drip irrigation every three weeks (three times). In a 15.6 acre test plot compared to a 73.2 acre control plot, the treated acreage gave about 29% higher yield than control (FIG. 6C).

Figure 6D:
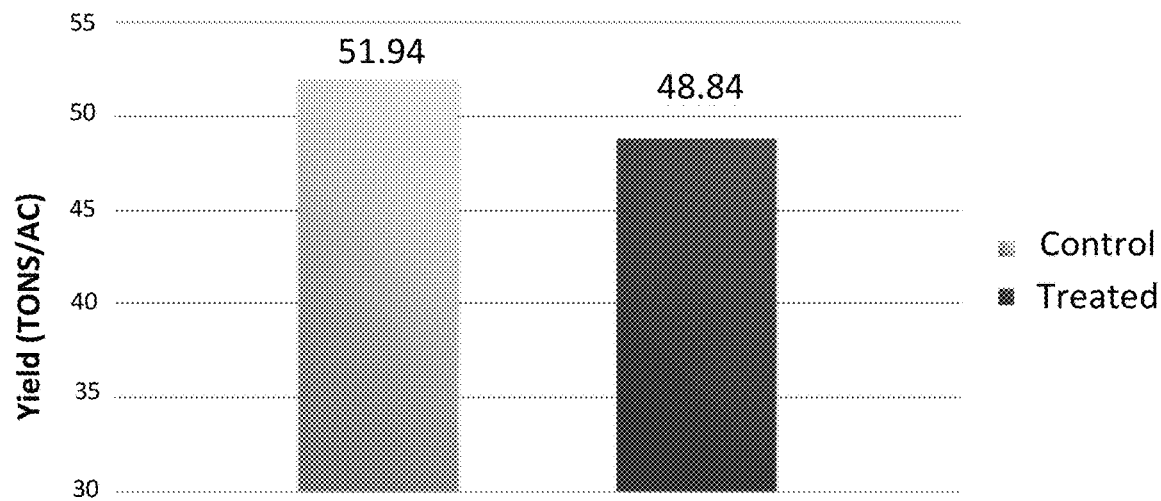

Trial 4 evaluated microbial composition treatment of tomato applied at 1 L/acre with by drip irrigation every three weeks (four times). In an 8.7 acre test plot compared to a 6.57 acre control plot, the treated acreage gave decreased yield compared to control (FIG. 6D). However, the trial was affected by severe disease pressure (*Fusarium*) which likely affected the outcome of the trial. In addition, this trial was a relatively small plot size and also included different crop varieties in the treatment.

Figure 6E:
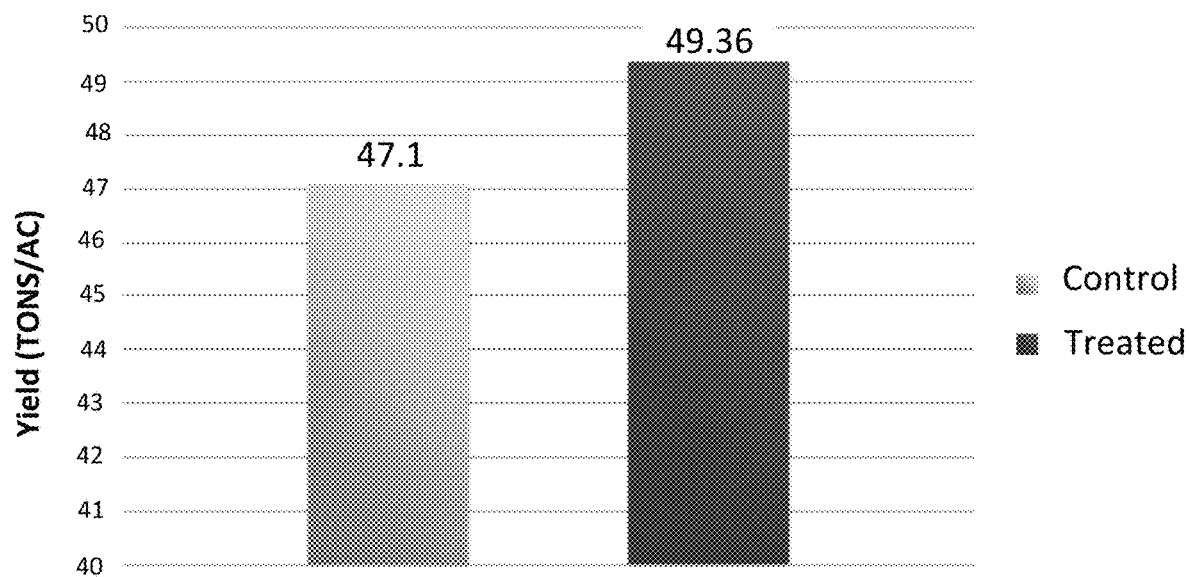

Trial 5 evaluated microbial composition treatment of tomato applied at 1 L/acre in combination with fertilizer treatment. One application was at transplant with 8-7-7, followed by application by drip irrigation every three weeks (three times) with UAN. In a 33.3 acre test plot compared to a 16.45 acre control plot, the treated acreage gave about 5% higher yield than control (FIG. 6E).

Example 10

Treatment of Sunflower with Microbial Compositions

This example describes a representative method for obtaining increased sunflower crop yield, using a microbial consortium. One skilled in the art will appreciate that methods that deviate from these specific methods can also be used for increasing crop yield.

Treatment of sunflower crop with a microbial composition prepared similarly to A1002 showed a strong increase in final harvestable yield. All agronomic practices of fertilization, cultivation, weed control, and pest control, were identical and side-by-side for both the microbial composition-treated (Test) and control (Check) plots.

Figure 7:
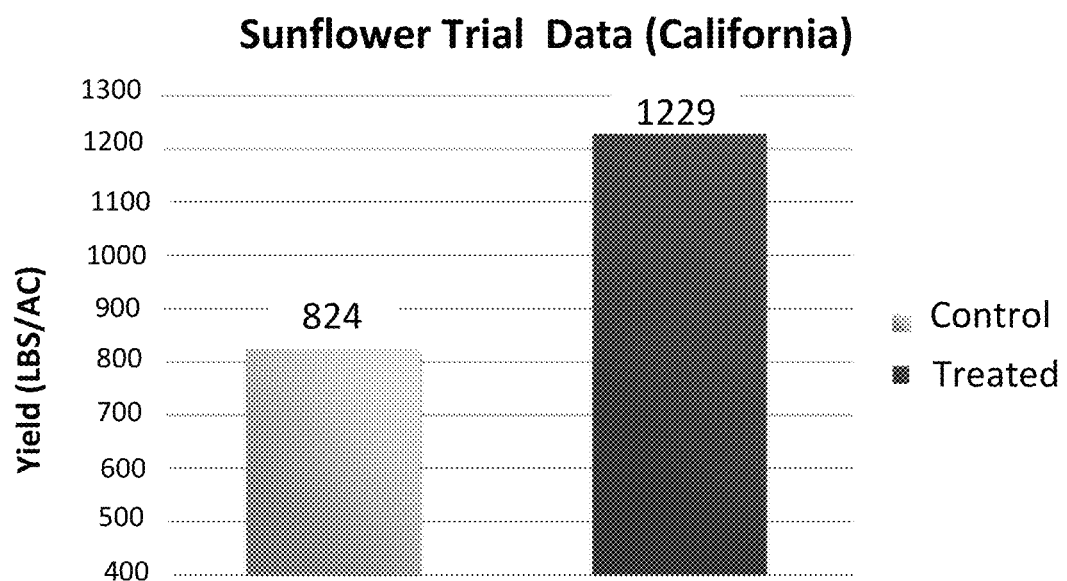
FIG. 7 is a graph showing the effect on yield of treatment of sunflower with a microbial composition.

This trial evaluated microbial composition treatment of sunflower applied at 1 L/acre by drip irrigation 30 days and 60 days post-planting. In a 93.5 acre test plot compared to a 97.13 acre control plot, the treated acreage gave about 50% higher yield than control (FIG. 7). In addition, the treatment resulted in increased germination rates.

Example 11

Treatment of Rice with Microbial Compositions

This example describes a representative method for obtaining increased rice crop yield, using a microbial consortium. One skilled in the art will appreciate that methods that deviate from these specific methods can also be used for increasing crop yield.

Treatment of rice with a microbial composition prepared similarly to A1002 showed a strong increase in final harvestable yield. All agronomic practices of fertilization, cultivation, weed control, and pest control, were identical and side-by-side for both the microbial composition-treated (Test) and control (Check) plots.

Figure 8:
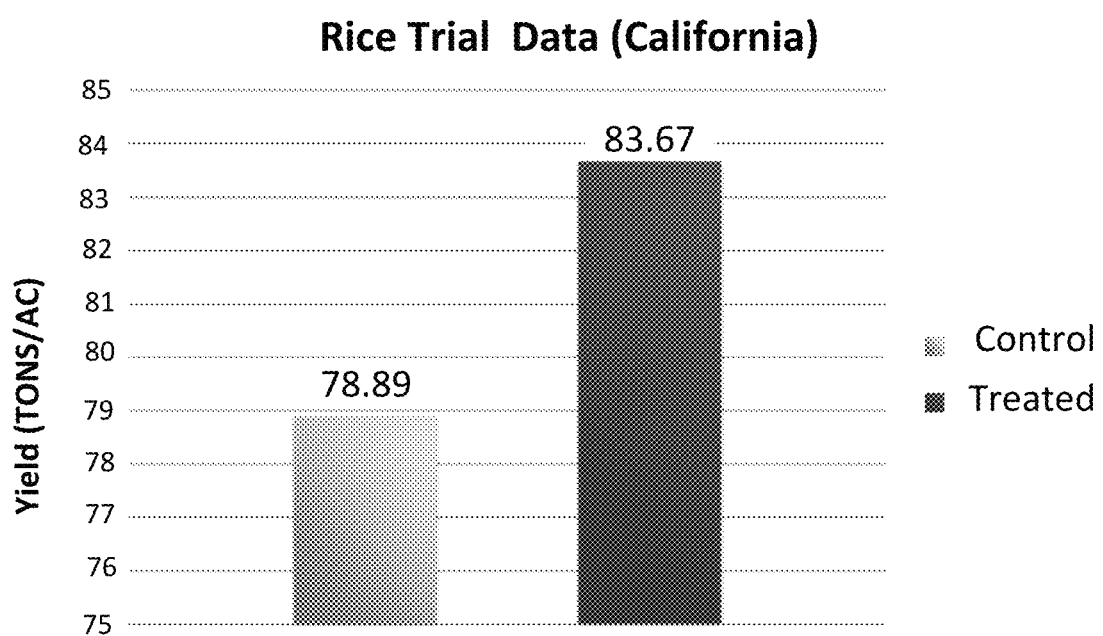
FIG. 8 is a graph showing the effect on yield of treatment of rice with a microbial composition.

This trial evaluated microbial composition treatment of rice applied at 1 L/acre with aqua ammonia. In a 61.8 acre test plot compared to a 100.7 acre control plot, the treated acreage gave about 6% higher yield than control (FIG. 8).

Example 12

Treatment of Soybean with Microbial Compositions

This example describes a representative method for obtaining increased soybean crop yield, using a microbial consortium. One skilled in the art will appreciate that methods that deviate from these specific methods can also be used for increasing crop yield.

Treatment of soybean with a microbial composition prepared similarly to A1002, or with HYTb, showed a strong increase in final harvestable yield. All agronomic practices of fertilization, cultivation, weed control, and pest control, were identical and side-by-side for the microbial composition- or HYTb-treated plots (Test) and control (Check) plots.

Figure 9A:
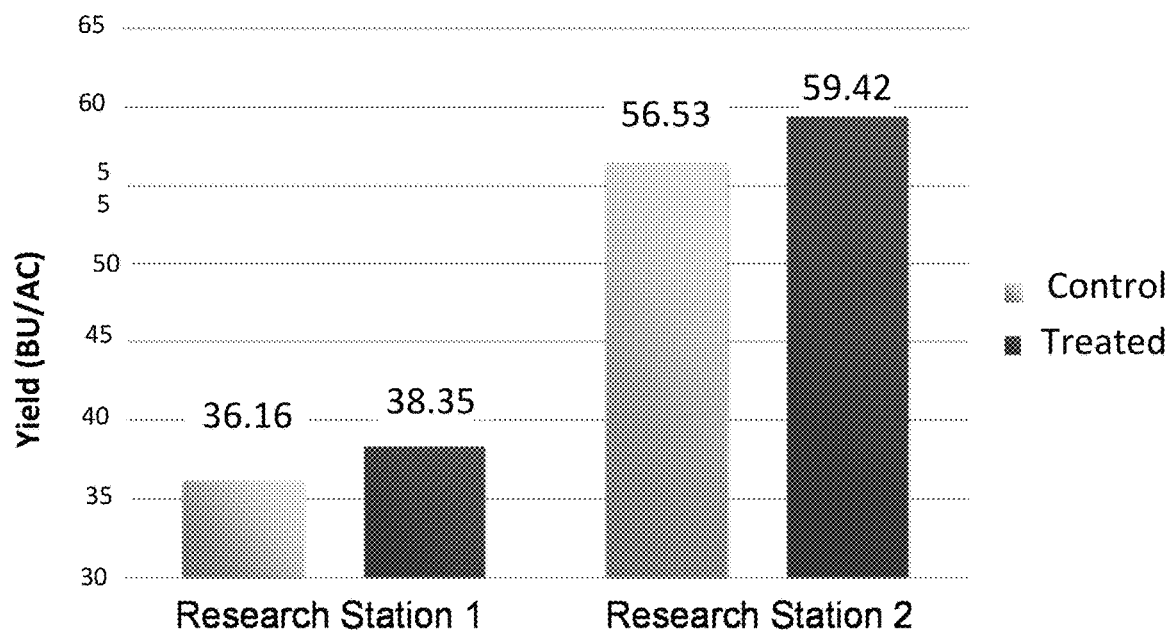
FIGS. 9A-9B show the effect on yield of treatment of soybean with a microbial composition (FIG. 9A) or with a microbial composition plus HYTb (FIG. 9B).

Trial 1 showed an increase in soybean yield promoted by application of HYTb at 1 L/acre, applied with fungicide. In two one acre tests, the treated acreage gave about 5% increased yield compared to control (FIG. 9A).

Figure 9B:
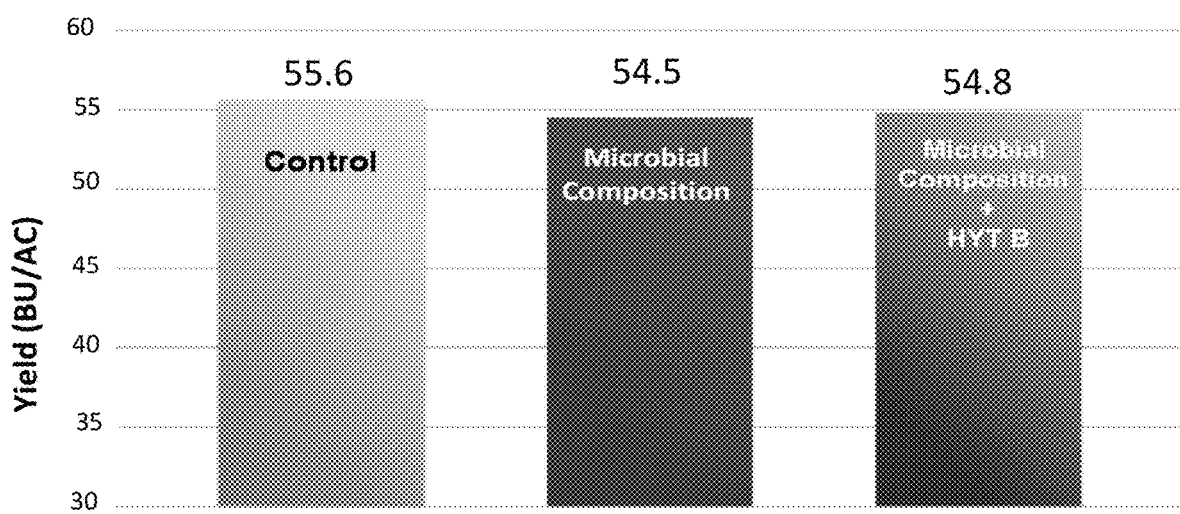

Trial 2 evaluated microbial composition treatment or microbial composition plus HYTb treatment of soybean applied at 1 L/acre by foliar and side dress application. The treated acreage had reduced yield compared to control (FIG. 9B). However, the trial was affected by small plot size combined with wildlife problems (deer nested and consumed the beans before harvest).

Trial 3 showed an increase in soybean yield promoted by application of HYTb at 0.5 L/acre, applied with fungicide by foliar application. In a 60 acre test plot compared to a 26.48 acre control plot, the treated acreage gave about 12% increased yield compared to control.

Example 13

Treatment of Strawberry with Microbial Compositions

This example describes a representative method for obtaining increased strawberry crop yield, using a microbial consortium. One skilled in the art will appreciate that methods that deviate from these specific methods can also be used for increasing crop yield.

Treatment of strawberry with a microbial composition prepared similarly to A1002 plus HYTb showed increases in final harvestable yield. All agronomic practices of fertilization, cultivation, weed control, and pest control, were identical and side-by-side for both the treated (Test) and control (Check) plots.

Figure 10:
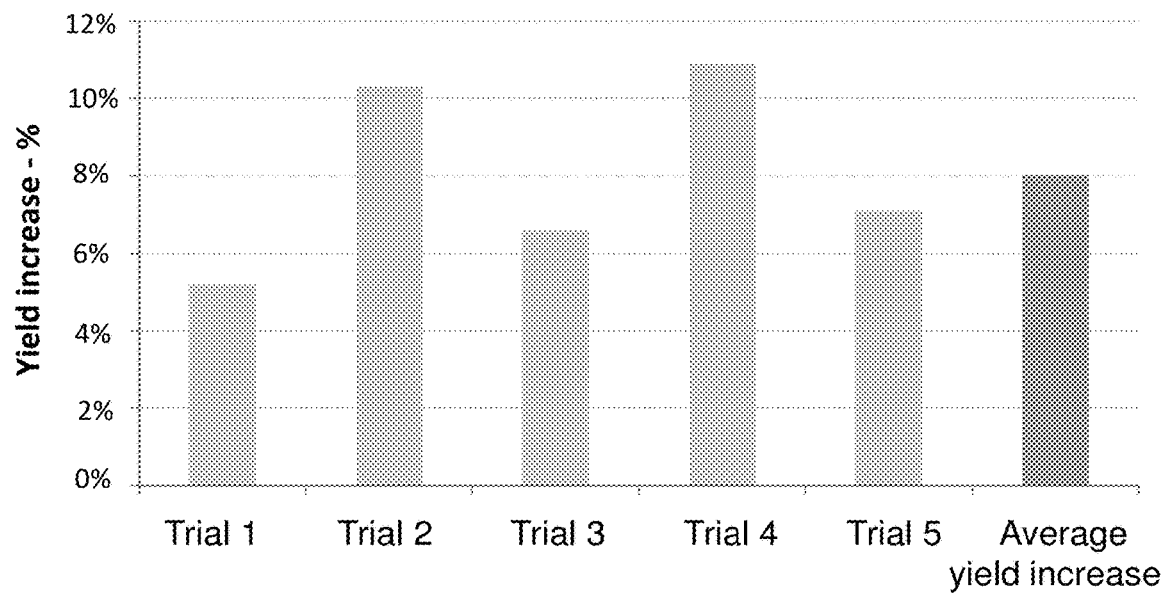
FIG. 10 is a graph showing the effect on yield of treatment of strawberry with a microbial composition plus HYTb.

An increase in cumulative marketable production was promoted by application of microbial composition and HYTb applied by drip irrigation. In these five independent trials, the Sabrina variety was evaluated in the Huelva region of Spain. One week prior to plantlet transplantation in the raised bed plots, 2 L of the microbial composition plus 4 L HYTb were diluted in water and added to the drip irrigation per hectare, with the same application rate performed at weeks 2, 4, and 6 post-planting. At weeks 3, 5, and 7, diluted microbial composition was added at a rate of 1 L/ha and diluted HYTb at a rate of 2 L/ha. From week 9 to the end of the harvest season, diluted microbial composition and HYTb were added at rates of 1 L/ha each. In all five trials, the treatment boosted yield from 5% to 11% above parallel non-treated plots, for an average of about an 8% yield increase across all five trials (FIG. 10).

Example 14

Treatment of Beetroot with Microbial Compositions

This example describes a representative method for obtaining increased beetroot crop yield, using a microbial consortium. One skilled in the art will appreciate that methods that deviate from these specific methods can also be used for increasing crop yield.

Treatment of beetroot with a microbial composition prepared similarly to A1002 plus HYTb showed increases in final harvestable yield. All agronomic practices of fertilization, cultivation, weed control, and pest control, were identical and side-by-side for both the treated (Test) and control (Check) plots.

Figure 11:
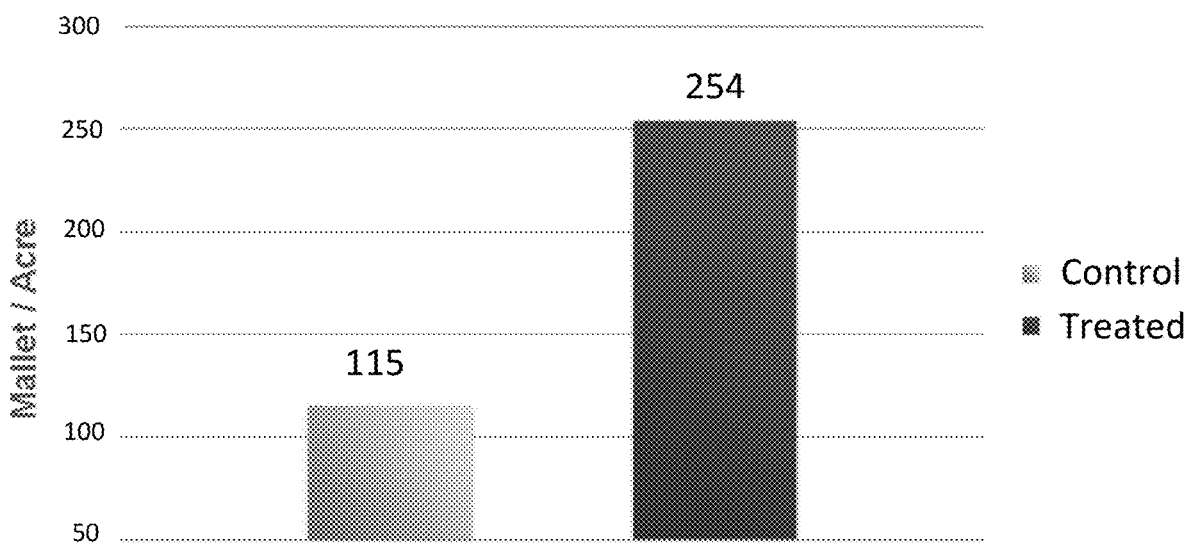
FIG. 11 is a graph showing the effect on yield of treatment of beetroot with a microbial composition plus HYTb.

An increase in average harvested head weight was promoted by application of microbial composition (2 L/acre) and HYTb (2 L/acre) applied by drip irrigation and HYTb (1 L/acre) by foliar application. In an 8 acre test plot compared to a 9 acre control plot, the treated acreage gave about 2.2-fold higher yield than control (FIG. 11).

Example 15

Treatment of Green Cabbage with Microbial Compositions

This example describes a representative method for obtaining increased green cabbage crop yield, using a microbial consortium. One skilled in the art will appreciate that methods that deviate from these specific methods can also be used for increasing crop yield.

Treatment of green cabbage with a microbial composition prepared similarly to A1002, or with HYTb, showed a strong increase in final harvestable yield. All agronomic practices of fertilization, cultivation, weed control, and pest control, were identical and side-by-side for the microbial composition- or HYTb-treated plots (Test) and control (Check) plots.

Figure 12A:
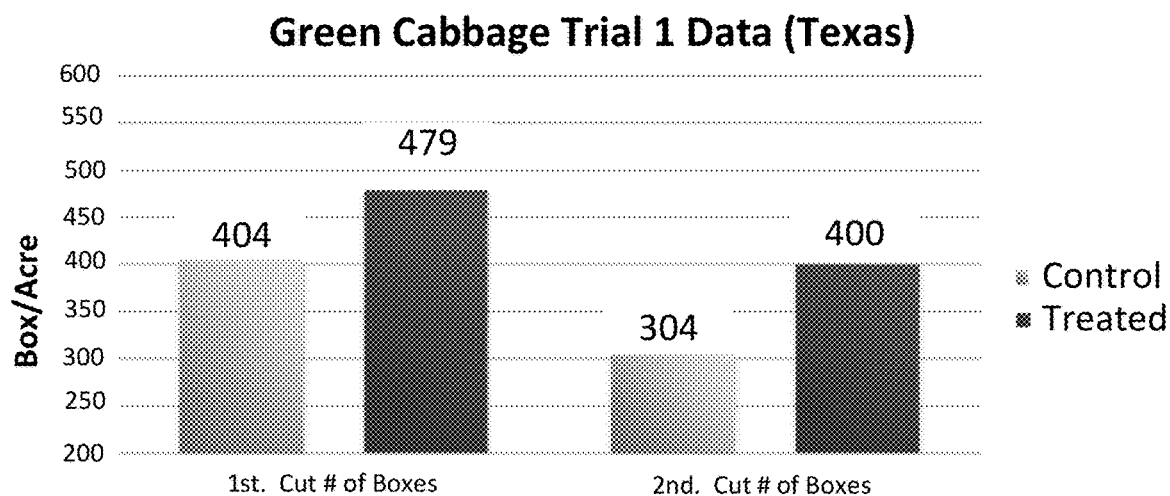
FIGS. 12A and 12B are graphs showing the effect on yield of treatment of green cabbage with a microbial composition plus HYTb in two trials (FIGS. 12A and 12B, respectively).
Figure 12B:
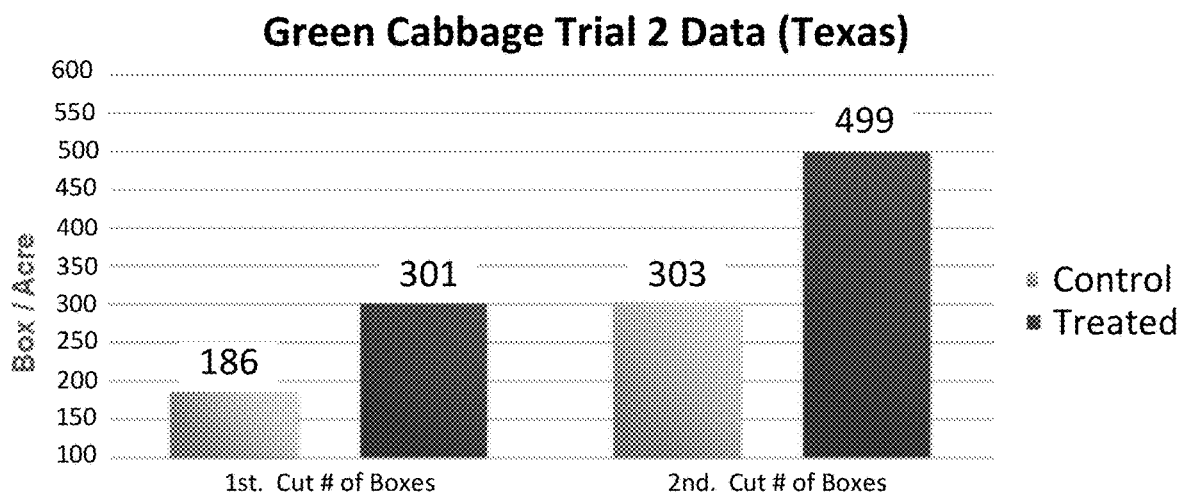

The trials showed an increase in cabbage yield promoted by application of microbial composition (2 L/acre) and HYTb (2 L/acre) applied by drip irrigation and HYTb (1 L/acre) by foliar application. Cabbages were harvested in two cycles, as represented by the "first cut" harvest of cabbage heads and the later "second cut" of cabbage heads. As shown in FIG. 12A, in a 10.9 acre test plot compared to a 14.9 acre control plot, the treated acreage gave about 18% higher yield than control (first cut) and about 31% higher yield than control (second cut). As shown in FIG. 12B, in a 3.7 acre test plot compared to a 1.5 acre control plot, the treated acreage gave about 61% higher yield than control (first cut) and about 64% higher yield than control (second cut).

Example 16

Seed and Tuber Treatment with HYTd

This example describes a representative method for obtaining increased wheat and potato crop yield using pre-treatment of the seed or seed tubers with HYTd. One skilled in the art will appreciate that methods that deviate from these specific methods can also be used for increasing crop yield.

Treatment of wheat seed or potato seed tubers prior to planting with HYTd prepared using a microbial consortium similar to A1002 showed increases in final harvestable yield. All agronomic practices of fertilization, cultivation, weed control, and pest control, were identical and side-by-side for both the treated (Test) and control (Check) plots.

For wheat, seed was treated in a diluted suspension of HYTd, diluted at a rate of 3 mL of HYTd in water per kg of seed. After coating seed and allowing air drying, treated seed was planted and compared to identical plots of untreated seed. One acre parallel field plots showed about 22% increase in wheat harvested yield (Table 3).

Potato seed treatment was performed by diluting HYTd in water and treating potato seed at a rate of 1 mL per kg of seed. After air drying, the treated potato seed was planted in parallel with untreated control seed in 1200 meter, replicated plots. HYTd treated potato seed increased potato yield 32% to 35% in two separate trials (Table 4).

TABLE 3

Yield from HYTd treated wheat seed

| Treatment | Dose (ml/kg seed) | Straw weight/ 5 m$^2$ area (kg) | Weight of grains/ 5 m$^2$ area (kg) | Yield (kg/acre) |
|---|---|---|---|---|
| HYTd | 3.00 | 9.8 | 2.6 | 1980 |
| Untreated | N/A | 5.5 | 1.7 | 1610 |

TABLE 4

Yield from HYTd treated potato seed

| Treatment | Dose (ml/kg seed) | Number of tubers/plant | Weight of tubers/m$^2$ (kg) | Final Yield (kg/acre) | % increase tuber yield |
|---|---|---|---|---|---|
| Trial 1 | | | | | |
| HYTd | 1.00 | 11 | 3.15 | 12448 | 32 |
| Untreated | N/A | 6 | 1.68 | 9440 | 0 |
| Trial 2 | | | | | |
| HYTd | 1.00 | 8 | 2.52 | 10720 | 35 |
| Untreated | N/A | 5 | 1.47 | 7932 | 0 |

Example 17

Increased Stress Tolerance in Potato

This example describes a representative method for obtaining increased potato tuber quality by treating with a microbial composition similar to A1002 and HYTb during growth under stressful field conditions.

Russet Burbank variety potato was grown under conventional conditions in a replicated plot trial (four replicates) and either treated (microbial composition plus HYTb at 1 L each per acre at planting, in furrow, followed by two foliar spray applications of HYTb at 1 L/acre at 55 days and again 85 days after planting) or untreated (control). Russet Burbank variety is prone to lower quality under water, heat, or nutrient stress. In this trial, the microbial composition and HYTb treatment enhanced tolerance to a stress-induced quality defect called hollow heart. Plots treated with microbial composition had an incidence of 1.68% of harvested tubers with hollow heart compared to the control with 8.35% hollow heart defects (Table 5).

TABLE 5

Potato hollow heart quality defects

| Treatment | Yield (kg/acre) | Hollow Heart percentage |
|---|---|---|
| Untreated (control) | 32,181 | 8.35% |
| Microbial composition plus HYTb | 32,636 | 1.68%* |

*$p < 0.01$ compared to untreated

Example 18

Cucumber Vigor Assay

Rapid plant-based functional assays can be used to quickly evaluate plant response to new microbial compositions. Using a cucumber vigor and plant growth assay, this example demonstrates that A1002 enhances the rate of plant leaf growth and expansion.

After pre-germination of cucumber seedlings in nutrient-soaked rolled germination paper for four days, staged and synchronized plants were treated with a diluted mixture of liquid fertilizer and microbial consortium. Plantlets were transplanted into prepared soilless growth medium pre-treated with fertilizer and the tester solution. The microbial composition A1002 was diluted 1:2000 in a nutrient fertilizer media. As control treatment, an equivalent amount of water added to nutrient media was compared. At least 16 plants of each treatment grown in pots, including control plants, were randomized in flats, and grown under defined growth conditions, controlling for temperature and light. After 18 days, the Leaf Area Index (LAI) of the first leaf of each plant was measured. The total plant wet weight was also recorded. The data was analyzed by One-way ANOVA (Analysis Of Variance) and with post-hoc Tukey test to compare samples within the experiment.

Figure 13:
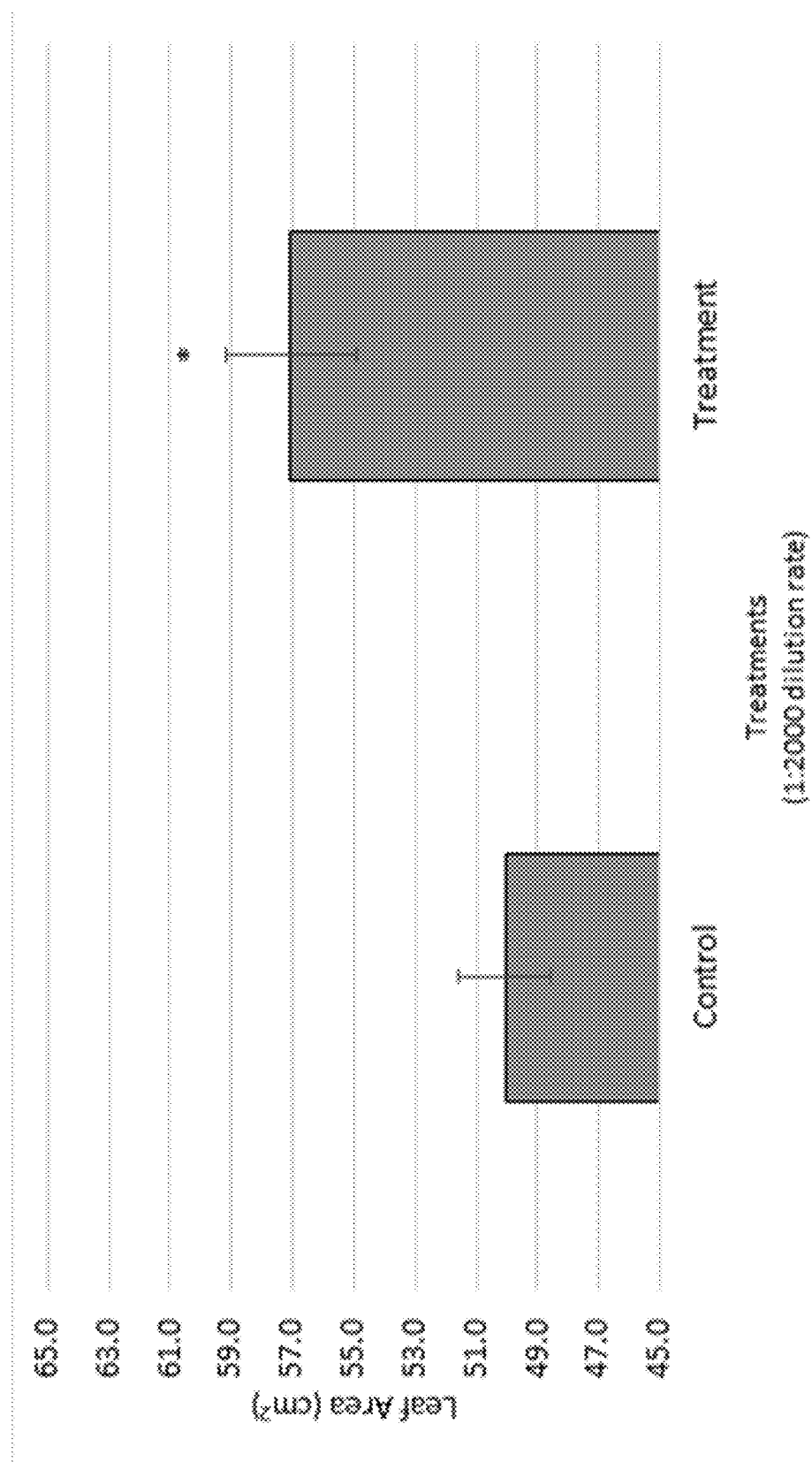
FIG. 13 is a graph of a cucumber vigor assay showing first leaf area index on day 18 in plants treated with A1002. *$p<0.01$ by ANOVA analysis.

At day 18, the first leaf LAI rating promoted by A1002 treatment was significantly greater than the control (FIG. 13).

In addition to, or as an alternative to the above, the following embodiments are described:

Embodiment 1 is directed to a composition comprising the microbes in ATCC deposit PTA-121751 (A1002).

Embodiment 2 is directed to a composition comprising five or more microbial species selected from *Bacillus* spp., *Azospirillum* spp., *Pseudomonas* spp., *Lactobacillus* spp., *Desulfococcus* spp., *Desulfotomaculum* spp., *Marinobacter* spp., *Nitrosopumilus* spp. *Ruminococcus* spp., *Aquabacterium* spp., *Acidisoma* spp., *Microcoleus* spp., *Clostridium* spp., *Xenococcus* spp., *Brevibacterium* spp., and *Methanosaeta* spp.

Embodiment 3 is directed to a composition comprising ten or more microbial species selected from *Bacillus* spp., *Azospirillum* spp., *Pseudomonas* spp., *Lactobacillus* spp., *Desulfococcus* spp., *Desulfotomaculum* spp., *Marinobacter* spp., *Nitrosopumilus* spp. *Ruminococcus* spp., *Aquabacterium* spp., *Acidisoma* spp., *Microcoleus* spp., *Clostridium* spp., *Xenococcus* spp., *Brevibacterium* spp., and *Methanosaeta* spp.

Embodiment 4 is directed to a composition comprising each of *Bacillus* spp., *Azospirillum* spp., *Pseudomonas* spp., *Lactobacillus* spp., *Desulfococcus* spp., *Desulfotomaculum* spp., *Marinobacter* spp., *Nitrosopumilus* spp. *Ruminococcus* spp., *Aquabacterium* spp., *Acidisoma* spp., *Microcoleus* spp., *Clostridium* spp., *Xenococcus* spp., *Brevibacterium* spp., and *Methanosaeta* spp.

Embodiment 5 is directed to a composition of any one of embodiments 1 to 4, further comprising one or more of chitin, chitosan, glucosamine, and amino acids.

Embodiment 6 is directed to a method comprising:
mixing a chitin-containing biological source with the composition of any one of embodiments 1 to 5 to form a mixture;
fermenting the mixture; and
separating the fermented mixture into solid, aqueous, and lipid fractions.

Embodiment 7 is directed to the method of embodiment 6, wherein the chitin-containing biological source comprises an aquatic animal or aquatic animal by-product, an insect, or a fungus.

Embodiment 8 is directed to the method of embodiment 7, wherein the aquatic animal is an aquatic arthropod.

Embodiment 9 is directed to the method of embodiment 8, wherein the aquatic arthropod is shrimp, crab, or krill.

Embodiment 10 is directed to the aqueous fraction made by the method of any one of embodiment 6 to 9.

Embodiment 11 is directed to a solid fraction made by the method of any one of embodiments 6 to 9.

Embodiment 12 is directed to a method comprising contacting soil, plants, or plant parts with the composition of any one of embodiments 1 to 5.

Embodiment 13 is directed to the method of embodiment 12, further comprising contacting the soil, plants, or plant parts with one or more of chitin, chitosan, glucosamine, and amino acids.

Embodiment 14 is directed to the method of embodiment 12 or 13, further comprising contacting the soil, plants, or plant parts with the aqueous fraction of claim 10 or the solid fraction of claim 11.

Embodiment 15 is directed to the method of any one of embodiments 12 to 14, further comprising contacting the soil, plants, or plant parts with a liquid fertilizer.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

---

---

We claim:

1. A method of improving plant growth and/or increasing crop yield, comprising contacting soil, plants, or plant parts with a microbial composition comprising ATCC Deposit number PTA-121751.

2. The method of claim 1, further comprising contacting the soil, plants, or plant parts with one or more of chitin, chitosan, glucosamine, and amino acids.

3. The method of claim 1, further comprising contacting the soil, plants, or plant parts with a liquid fertilizer.

4. The method of claim 1, further comprising contacting the soil, plants, or plant parts with one or more pesticides, one or more fungicides, one or more herbicides, one or more insecticides, one or more plant hormones, one or more plant elicitors, or combinations of two or more thereof.

5. The method of claim 1, further comprising contacting the soil, plants, or plant parts with an aqueous fraction and/or a solid fraction produced by a method comprising:

mixing a chitin-containing biological source with a microbial composition comprising microbial species selected from five or more of *Bacillus* spp., *Azospirillum* spp., *Pseudomonas* spp., *Lactobacillus* spp., *Desulfococcus* spp., *Desulfotomaculum* spp., *Marinobacter* spp., *Nitrosopumilus* spp. *Ruminococcus* spp., *Aquabacterium* spp., *Acidisoma* spp., *Microcoleus* spp., *Clostridium* spp., *Xenococcus* spp., *Brevibacterium* spp., and *Methanosaeta* spp. to form a mixture;

fermenting the mixture; and separating the fermented mixture into solid, aqueous, and lipid fractions.

6. The method of claim 1, further comprising activating the microbes prior to contacting soil, plants, or plant parts with the microbial composition.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 1
agrgtttgat cmtggctcag                                                 20

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 2
ggttaccttg ttacgactt                                                  19